United States Patent [19]
Yoshida et al.

[11] Patent Number: 5,963,328
[45] Date of Patent: Oct. 5, 1999

[54] SURFACE INSPECTING APPARATUS

[75] Inventors: Kiyoshi Yoshida; Yoshitaka Usui; Norikazu Tsubaki, all of Kanagawa-ken, Japan

[73] Assignee: Nissan Motor Co., Ltd., Kanagawa-ken, Japan

[21] Appl. No.: 09/143,522

[22] Filed: Aug. 28, 1998

[30] Foreign Application Priority Data

Aug. 28, 1997 [JP] Japan .................................. P9-232954
Sep. 30, 1997 [JP] Japan .................................. P9-266911

[51] Int. Cl.$^6$ .................................................. G01B 11/30
[52] U.S. Cl. ........................................ 356/371; 356/237.2
[58] Field of Search .................................... 356/371, 376, 356/237.1, 237.2, 237.3, 239.1, 239.2, 239.7, 239.8

[56] References Cited

U.S. PATENT DOCUMENTS 5,086,232   2/1992   Maguire et al. ......................... 356/376
5,606,410   2/1997   Peclier et al. ......................... 356/237.2

FOREIGN PATENT DOCUMENTS 6-3286   1/1994   Japan .
8-5573   1/1996   Japan .

*Primary Examiner*—Richard A. Rosenberger
*Attorney, Agent, or Firm*—McDermott, Will & Emery

[57] ABSTRACT

A surface inspecting apparatus includes linear light sources 11, 13 for emitting illumination light toward a surface of a body panel 10 to be inspected, CCD cameras 12, 14 for imaging the surface and forming its illuminated images on the basis of reflection light from the surface, and an inspecting unit for detecting a defect existing on the surface on a basis of the illuminated image and outputting detected information about the defect. In the arrangement, the sources 11, 13 are arranged so as to obliquely emit the illumination light toward the surface at incident angles $\alpha$ from 80 to 90 degrees. While, the cameras 12, 14 are arranged so as to receive diffused reflection light of the illumination light reflected by the surface at reflection angles $\beta$ each smaller than the incident angle $\alpha$.

16 Claims, 19 Drawing Sheets

CONVEYER REFERENCE SURFACE

SURFACE INSPECTING APPARATUS

BACKGROUND OF THE INVENTION

1. Field of the Invention

The present invention relates to a surface inspecting apparatus for inspecting a surface of an object to be inspected, for example a body panel constituting a body for a vehicle. More particularly, the present invention relates to a surface inspecting apparatus which is capable of inspecting the existence of surface defects such as irregularities on a surface of the body panel subjected to a press working.

2. Description of the Related Art

Japanese Unexamined Patent Publication (kokai) No. 8-5573 shows conventional surface inspecting apparatus. The surface inspecting apparatus disclosed in this publication is provided with an illuminating unit as a light source, for emitting light in the form of a plane to a surface of a workpiece as the object to be inspected. In arrangement, the illuminating unit is obliquely positioned upward one side of the workpiece. The apparatus further includes an area sensing camera as an imaging unit, which is obliquely positioned upward the other side of the workpiece, for capturing the reflected plane light to take a picture of the surface of the workpiece. In this way, alien substances and projections existing on the surface of the workpiece are detected by the above surface inspecting apparatus.

This publication also discloses another type of surface inspecting apparatus. This surface inspecting apparatus includes an illuminating unit for emitting light in the form of a line to the surface of the workpiece. In arrangement, the illuminating unit is obliquely positioned upward one side of the workpiece, too. Similarly to the previously-mentioned apparatus, the surface inspecting apparatus further includes a line sensing camera as the imaging unit, which is obliquely positioned upward the other side of the workpiece, for capturing the reflected linear light to take a picture of the surface of the workpiece. In this way, micro-projections etc. existing on the surface of the workpiece are detected by the surface inspecting apparatus. Note, in this specification, the illuminating unit for emitting light in the form of a line may be also referred as "linear light source".

In common with the above-mentioned surface inspecting apparatuses of different types, an incident angle $\alpha$ of the illumination light from each light source and a reflecting angle $\beta$ of the reflected light captured by each sensing camera are both included within a range from 80 to 90 degrees, being generally equal to each other. That is, both of the surface detecting apparatuses are adapted so as to capture the so-called regular reflection light (alias, specular reflection light) for a captured image. In this case, the alien substances and defects on the surface of the workpiece are imaged as various shadows, in detail, dark spots in a bright zone on a display.

As a reference, it is noted that Japanese Unexamined Patent Publication (kokai) No. 6-3286 discloses a large and complex surface inspecting apparatus with an "inverse" reflecting screen, which utilizes oil to be applied to the surface, for equalizing the gloss of surface thereby detecting the surface defects stably.

SUMMARY OF THE INVENTION

In the surface inspecting apparatus of the Publication No. 8-5573, as mentioned above, the incident angle $\alpha$ of the illumination light and the reflecting angle $\beta$ of the reflection light are included within the range from 80 to 90 degrees and additionally, the specular reflection light is used for detecting the surface defects, in other words, the incident angle $\alpha$ is substantially equal to the reflecting angle $\beta$ (i.e. $\alpha=\beta$). Therefore, for example, when it is required in a production line to inspect the existence of irregularities having relatively gentle angles of inclination, projections or the like, from the curved surface of the body panel as the objected to be inspected, there arises various problems as follows.

That is, since the inspection is carried out at a small imaging angle ($90°-\beta$) which is less than 10 degrees, in case of the former detecting apparatus, then such an inspection causes the detection range of the area sensing camera to be extremely narrowed because of its restricted depth of field. In addition, the imaging range of the camera is extremely increased in one direction only, so that the resolving power of the camera is deteriorated. Thus, the captured images of the defects are distorted, thereby causing the difficulty to detect the defects with high accuracy and reliability.

Additionally, as it is general that the body panel is shaped so as to have a curved surface (e.g. a surface with radius of curvature R), it is difficult to maintain the above-mentioned appropriate angular condition of the incident angle $\alpha$ and the reflecting angle $\beta$, in other words, the condition of the emitting angle ($90°-\alpha$) and the imaging angle ($90°-\beta$), on the surface of the body panel. Thus, it is impossible to install the surface inspecting apparatus in the production line.

It is therefore an object of the present invention to provide a surface inspecting apparatus which can be installed in the production line and which is capable of detecting the surface defects, such as irregularities and projections having relatively gentle angles of inclination, on the curved surface of the body panel with high accuracy and reliability. Another object of the present invention is to provide a surface inspecting apparatus which is capable of surely detecting the surface defects on the surface to be inspected including oil-sticking surface and curved face.

The above object of the present invention described above can be accomplished by a surface inspecting apparatus for inspecting a surface of an object to be inspected, the surface inspecting apparatus comprising:

an illuminating unit for emitting illumination light to the surface of the object;

an imaging unit for taking a picture of the surface of the object illuminated by the illumination light, thereby to form an illuminated image of the surface;

an image processing unit for detecting a defect existing on the surface on a basis of the illuminated image obtained by the imaging unit, thereby to output detected information about the defect;

a surface-sort inputting unit for inputting a sort of the surface to be inspected;

a surface-position detecting section for detecting positional information about a position of the surface in a transporting direction to transport the object;

a surface-information specifying section for specifying a curved profile of the surface and angular information about an angle of inclination of the surface, corresponding to the sort of the surface obtained by the surface-sort inputting unit and the positional information obtained by the surface-position detecting section; and positional relationship controlling section for controlling a positional relationship among the illuminating unit, the imaging unit and the surface to be inspected, on the basis of the angular information specified by the surface-information specifying section and the positional information detected by the surface-position detecting section;

wherein the positional relationship controlling section controls the positional relationship among the illuminating unit, the imaging unit and the surface to be inspected in such a manner that an incident angle of the illumination light on the surface falls within a definite range and the imaging unit receives diffused reflection light of the illumination light reflected by the surface at a reflection angle which is smaller than the incident angle of the illumination light.

According to the surface inspecting apparatus constructed above, for example, the incident angle α of the illumination light emitted by the illuminating unit is established within a range from 80 to 90 degrees, in other words, the emitting angle (90°−α) is established close to the level so as to be equal to or less than 10 degrees. While, the reflection angle β of the reflection light received by the imaging unit is established within, for example an range from 50 to 75 degrees, which is smaller than the incident angle α. Thus, the imaging angle (90°−β) is established to an intermediate angle from 15 to 40 degrees, which is larger than the emitting angle (90°−α). Consequently, since the illumination light is emitted at small angles close to the level, it is possible to capture the diffused reflection light due to surface defects, with high luminance (brightness). Hereat, the surface defects are defined as, for example gentle irregularities and projections etc. reflecting the illumination light at respective reflection angles each smaller than that of the specular reflection light due to disturbance surface except the defects, in the reflection lights exhibiting high reflectivity.

Therefore, it is preferable that in the surface inspecting apparatus, the incident angle of the illumination light is from 80 to 90 degrees, while the reflection angle of the diffused light is from 50 to 75 degrees.

In order to realize the above-mentioned establishment in the incident angle and the reflection angle, it is preferable that the positional relationship controlling section in the surface inspecting apparatus comprises:

an emitting angle and position controlling section for controlling both of an emitting angle of the illuminating unit and a height thereof so that the incident angle of the illumination light on the surface falls within the definite range usually; and an imaging angle and position controlling section for controlling both of an imaging angle of the imaging unit and a height thereof so that the imaging unit receives the diffused reflection light of the illumination light reflected at the reflection angle smaller than the incident angle of the illumination light.

More preferably, the surface inspecting apparatus further comprises a setting angle inputting unit into which a setting inclination angle of the object when the object is transported and the surface-information specifying section specifies the curved profile of the surface and the angular information about the angle of inclination of the surface, corresponding to the sort of the surface obtained by the surface-sort inputting unit, angular information of the object obtained by the setting angle inputting unit and the positional information obtained by the surface-position detecting section.

With the above constitution of the surface inspecting apparatus, when inspecting the object to be transported at a predetermined speed (e.g. the body panel in a production line), it would be possible to convey the body panel without stopping the production line and successively detect the gentle irregularities and the projections etc. with high accuracy and reliability.

It is also preferable that the illuminating unit in the surface inspecting apparatus includes a front illuminating unit for illuminating a front side of the surface to be inspected in the transporting direction and a rear illuminating unit for illuminating a rear side of the surface to be inspected in the transporting direction, while the imaging unit includes a front imaging unit for taking a picture of the front side of the surface in the transporting direction on the basis of the reflection light from the surface and a rear imaging unit for taking a picture of the rear side of the surface in the transporting direction on the basis of the reflection light from the surface, and that the surface inspecting apparatus further comprises a front-to-back illuminating and imaging switching section which carries out a switching in operation between the front illuminating unit and the rear illuminating unit and another switching in operation between the front imaging unit and the rear imaging unit.

With the above constitution of the surface inspecting apparatus, if the surface of the object to be inspected is contoured of an upward convex profile having a top at an intermediate portion thereof and downward inclinations on both sides of the top, such as a general body panel, then it is possible to inspect the surface while switching an operation by the couple of the illuminating unit and the imaging unit between the front side area of the object and the rear side area.

Therefore, it is possible to establish the emitting angle (90°−α) and the imaging angle (90°−β) within the above-mentioned desired ranges respectively, whereby the surface defects such as gentle irregularities and the projections etc., can be detected over the whole area of the surface to be inspected, with high accuracy and reliability.

In the above-mentioned surface inspecting apparatus, preferably, the illuminating unit is constituted by a linear light source and the imaging unit is constituted by a CCD camera.

In this case, owing to the provision of the linear light source and the CCD camera, it is possible to detect the surface defects, such as gentle irregularities and the projections etc., on the curved surface of the body panel having low glossiness, with high accuracy and reliability.

In the above-mentioned surface inspecting apparatus, preferably, at least either one of the illuminating unit and the imaging unit has a light-quantity adjusting function which is capable of coping with respective reflectivities of light at an oil-sticking portion and a non-sticking portion on the surface of the object.

Generally speaking, a pressed product of steel such as a body panel etc., has oil such as anticorrosive oil, cleaning oil etc. sticking on the surface locally. Further, it should be noted that the reflectivity of such an oil-sticking portion is smaller than that of a non-sticking portion and-therefore, the detection sensitivity of the image processing unit against the oil-sticking portion is about one-fourth of that against the non-sticking portion.

Therefore, according to the above-mentioned surface inspecting apparatus, it is executed to capture the surface to be inspected while adjusting the light value of at least one of the illuminating unit and the imaging unit, corresponding to the respective reflectivities of the oil-sticking portion and the non-sticking portion. That is, when imaging with the light-value adjustment (light value: large/iris: small) corresponding to the reflectivity of the oil-sticking portion, then the non-sticking portion is not captured clearly because of its saturated state, while the oil-sticking portion is captured clearly. This is because the reflectivity of the oil-sticking portion is smaller than that of the non-sticking portion. On the contrary, when imaging with the light-value adjustment (light value: small/iris: large) corresponding to the reflectivity of the non-sticking portion, then the non-sticking portion is captured clearly, while the oil-sticking portion is not captured clearly due to lacking in quantity of light (light value).

Thus, since the images are captured in the above way and then the so-obtained images of the oil-sticking portion and the non-sticking portion are formed to extract the surface defects for each image in the inspecting unit, it is possible to detect the existence of the surface defects.

Further, owing to the above-mentioned adjustment of light value in the illuminating unit and/or the imaging unit, the surface inspecting apparatus can be simplified in structure and down-sized in comparison with the conventional inspecting apparatuses employing, for example an inverse-reflection screen, an oil painting unit or the like. Consequently, it is possible to cope with the installation of the apparatus into the pressing line for the body panel etc., with ease and low cost. Furthermore, in spite of the surface having oil partially sticking thereon, it is possible to inspect the existence of surface defects on the surface as it is, certainly. Additionally, since there is no need to apply oil on the surface newly, the inspection for defects can be accomplished on even a curved surface to be inspected, certainly.

In the above-mentioned surface inspecting apparatus, more preferably, the imaging unit comprises a first camera having an iris (small) adjusted corresponding to the reflectivity of light at the oil-sticking portion and a second camera having an iris (large) adjusted corresponding to the reflectivity of light at the non-sticking portion and the first and second cameras are so arranged as to respectively provide first and second imaging positions in series along the transporting direction of the surface to be inspected.

In this case, the oil-sticking portion and the non-sticking portion can be successively captured with the movement of the surface to be inspected. Furthermore, owing to the imaging unit consisting of the first and second cameras of different irises, it is possible to image the oil-sticking portions and the non-sticking portions on the surface moving to one direction at a constant speed, individually and certainly, thereby allowing the surface defects on the body panel to be automatically detected with high detection ratio, for example in the pressing line for the body panel.

Alternatively, it is also preferable that the imaging unit comprises first and second cameras arranged as to respectively provide first and second imaging positions in series along the transporting direction of the surface to be inspected, while the illuminating unit comprises a first illuminating part having a quantity of light (large) adjusted corresponding to the reflectivity of the oil-sticking portion and a second illuminating part having a quantity of light (small) adjusted corresponding to the reflectivity of the non-sticking portion and that the first and second illuminating parts are arranged so that first and second illuminating positions thereof correspond to the first and second imaging positions, respectively.

Also in this case, the oil-sticking portion and the non-sticking portion can be successively captured with the movement of the surface to be inspected. Furthermore, owing to the first and second cameras and the first and second illuminating parts of different quantities of light (different light values), it is possible to image the oil-sticking portions and the non-sticking portions on the surface moving to one direction at a constant speed, individually and certainly, thereby allowing the surface defects on the body panel to be automatically detected with high detection ratio, for example in the pressing line for the body panel.

In the surface inspecting apparatus, preferably, the image processing unit has a function to combine a defect-image extracted from the oil-sticking portion with another defect-image extracted from the non-sticking portion.

In such a case, the existence of the surface defects is identified in the integrated image of the surface to be inspected finally. Therefore, an operator's work for identifying the surface defects can be facilitated.

More preferably, the positional relationship controlling section in the surface inspecting apparatus comprises a surface angle and position control section for controlling an inclination angle and a height of the surface to be inspected in such a manner that both of the emitting angle of the illuminating unit and the imaging angle of the imaging unit usually fall within definite ranges, respectively.

Also in this case, when inspecting the object to be transported at a predetermined speed (e.g. the body panel in a production line), it would be possible to convey the body panel without stopping the production line and successively detect the gentle irregularities and the projections etc. with high accuracy and reliability.

In the above arrangement, the illuminating unit may comprise the linear light source and the imaging unit may comprise the CCD camera.

In the above arrangement, more preferably, at least either one of the illuminating unit and the imaging unit has a light-quantity adjusting function which is capable of coping with respective reflectivities of light at the oil-sticking portion and the non-sticking portion on the surface of the object.

Alternatively to the above arrangement, the imaging unit may comprise a first camera having an iris adjusted corresponding to the reflectivity of light at the oil-sticking portion and a second camera having an iris adjusted corresponding to the reflectivity of light at the non-sticking portion and furthermore, the first and second cameras may be so arranged as to respectively provide first and second imaging positions in series along the transporting direction of the surface to be inspected.

Or again, the imaging unit may comprise first and second cameras arranged as to respectively provide first and second imaging positions in series along the transporting direction of the surface to be inspected, while the illuminating unit comprises a first illuminating part having a quantity of light adjusted corresponding to the reflectivity of the oil-sticking portion and a second illuminating part having a quantity of light adjusted corresponding to the reflectivity of the non-sticking portion and the first and second illuminating parts may be arranged so that first and second illuminating positions thereof correspond to the first and second imaging positions, respectively.

Similarly, it is also preferable that, in the above-mentioned arrangement, the inspecting unit may has a function to combine a defect-image extracted from the oil-sticking portion with another defect-image extracted from the non-sticking portion.

The above and other features and advantages of this invention will become apparent, and the invention itself will best be understood, from a study of the following description and appended claims, with reference had to the attached drawings showing a preferred embodiment of the invention.

BRIEF DESCRIPTION OF THE DRAWINGS

FIG. 9A shows a condition to illuminate and image the front side of a surface to be inspected, while FIG. 9B shows a condition to illuminate and image the rear side of the surface;

DESCRIPTION OF THE PREFERRED EMBODIMENT

Embodiments of the present invention will be described with reference to the drawings.

Figure 1:
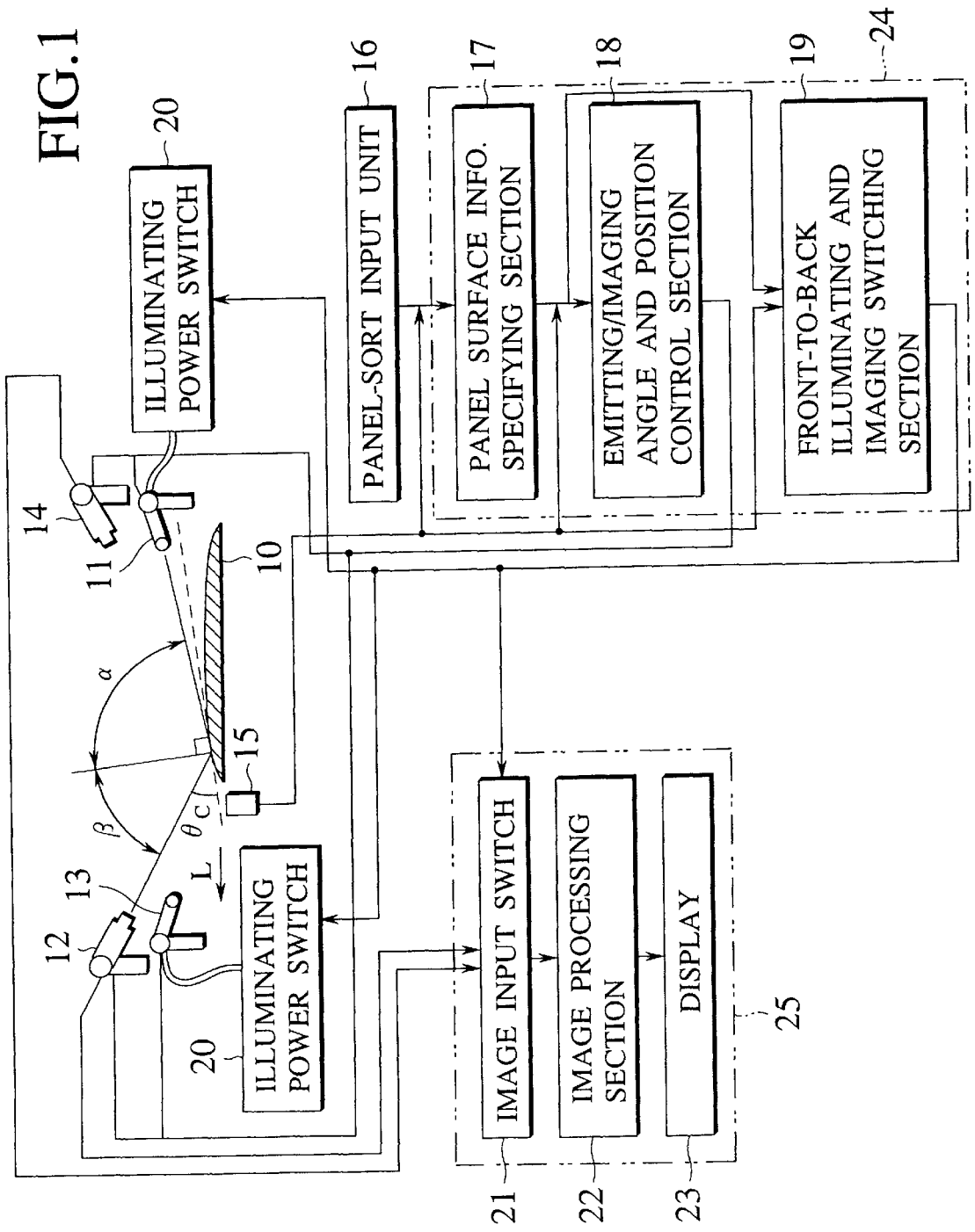
FIG. 1 is a schematic view showing a constitution of a surface inspecting apparatus in accordance with a first embodiment of the present invention.

FIG. 1 show a constitution of a surface inspecting apparatus in accordance with a first embodiment of the present invention. Note, in the embodiment, the surface inspecting apparatus is directed to detect surface defects on a surface of a body panel for a vehicle, which has been subjected to press working. As shown in FIG. 1, the surface inspecting apparatus basically includes a linear light source 11 as a front illuminating unit which emits the illumination light on a front side of a body panel 10 as an object to be inspected, in a transporting direction (L) thereof, a CCD (charge coupled device) camera 12 as a front imaging unit which receives reflection of the illumination light emitted from the linear light source 11 to form an illuminated image from the reflection light, another linear light source 13 as a rear illuminating unit which emits illumination light on the rear side of the body panel 10 in the transporting direction (L), another CCD camera 14 as a rear imaging unit which receives the reflection of the illumination light emitted from the linear light source 13 to form another receipt image from the reflection light, and a panel position detecting sensor 15 as a detecting unit for detecting positional information of the surface to be inspected. In detail, when the body panel 10 is transported by a not-shown belt conveyer or the like, the panel position detecting sensor 15 detects a position of the surface of the body panel 10 in the transporting direction (L).

According to the embodiment, each of the linear light sources 11, 13 is arranged obliquely upward one side of the body panel 10 and oriented in a manner that the incident angle α of the illumination light toward the surface of the panel 10 is within a range from 80 to 90 degrees (exactly, 80 degrees or more and under 90 degrees). It also means, in other words, that the emitting angle (90°−α) of each linear light source 11(13) is equal to or less than 10 degrees. While, each of the CCD cameras 12, 14 is arranged obliquely upward the other side of the body panel 10, thereby cooperating with the linear light sources 11, 13, respectively. Again, each of the CCD cameras 12, 14 is oriented so as to receive the diffused light reflected at the reflection angle β in the range from 50 to 75 degrees, which is smaller than the incident angle α. That is, each of the CCD cameras 12, 14 is oriented so that the imaging angle (90°−β) exhibits an intermediate angle in the range from 15 to 40 degrees.

Further, each of the linear light sources 11, 13 is provided with an adjusting mechanism for adjusting the height of emitting origin and emitting angle. Similarly, each CCD camera 12, 14 is also provided with an adjusting mechanism for adjusting the height of light-receiving point and imaging angle. Thus, the respective positions of the light sources 11, 13 and the CCD cameras 12, 14 are adjustable in a manner that predetermined emitting angle and predetermined imaging angle in the above-mentioned ranges are usually maintained with respect to the panel surface of which inclination angle changes with the transportation of the body panel 10.

By orientating the linear light sources 11, 13 and the CCD cameras 12, 14 in the above ranges of the emitting angle (90°−α) and the imaging angle (90°−β), the illumination light can be emitted at small angles close to just right (the level), while it is possible to capture the diffused reflection light due to the surface defects, such as gentle irregularities and projections etc., with high luminance (brightness). It is noted that these gentle irregularities and projections reflect the illumination light at respective reflection angles each smaller than that of the specular reflection light due to disturbance surface except the defects, in the reflection lights exhibiting high reflectivity.

Figure 2:
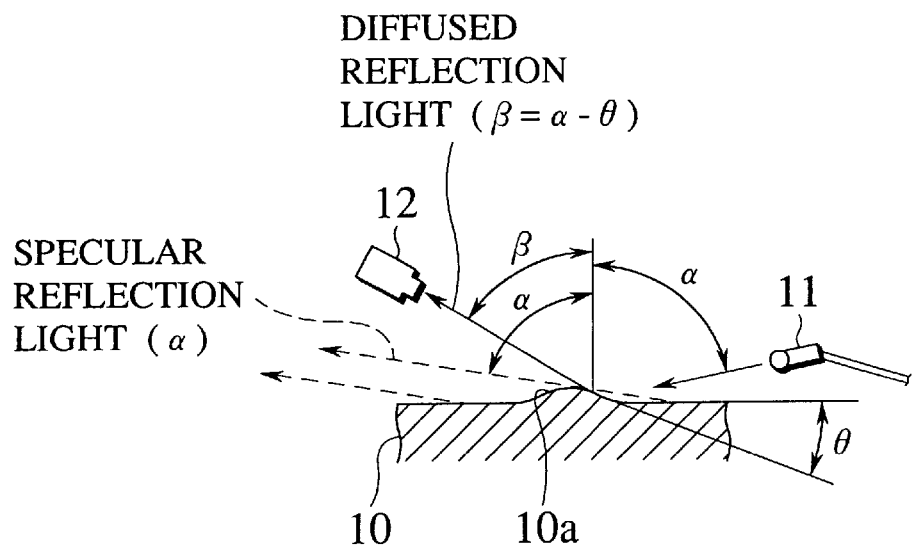
FIG. 2 is an explanatory diagram of the principle of inspection in the surface inspecting apparatus of the present invention.

We now explain a principle of the above-mentioned effect. As shown in FIG. 2, the illumination light is firstly emitted from the linear light source 11(13) toward the surface of the body panel 10 at the incident angle α. Then, the illumination light emitted on the disturbance surface (not a defect) is turned to the specular reflection light reflected at the reflection angle equal to the incident angle α, while the illumination light emitted on a convex detect 10a having the inclination angle θ is turned to the diffused reflection light reflected at the reflection angle β.

Then, since the emitting angle (90°−α) of the linear light source 11(13) exhibits a shallow angle being less than 10 degrees relative to the panel surface, the high reflectivity can be obtained owing to Sheen phenomenon where the orientation of reflected light distribution is enhanced. Therefore, it is possible to distinguish between the reflected light distribution at the reflection angle α by the disturbance surface excluding the defects and the reflected light distribution at the reflection angle β by the defects, clearly.

Figure 3:
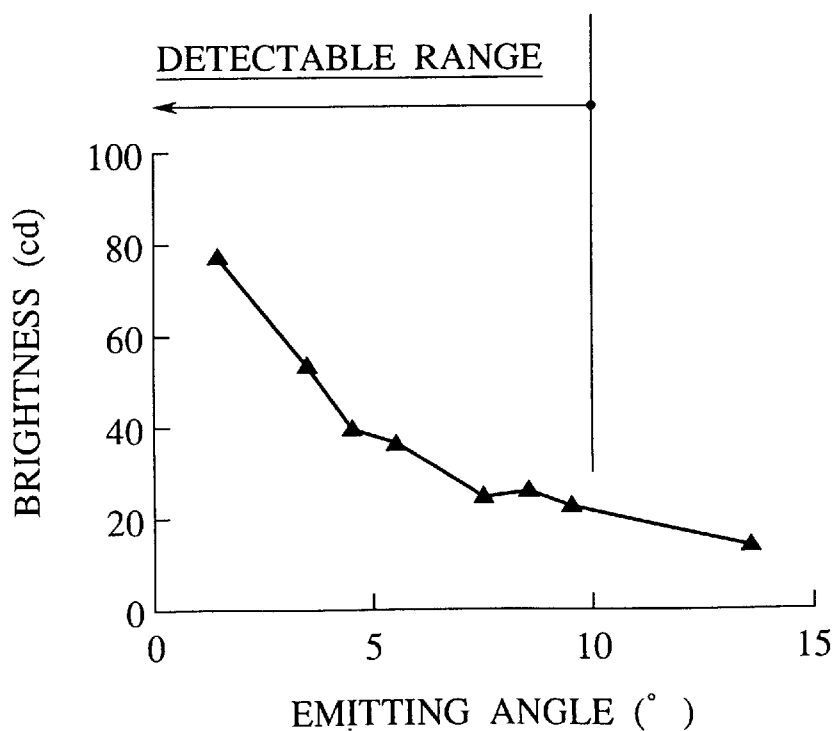
FIG. 3 is a graph showing a relationship between an emitting angle of illumination light by an illuminating unit and a brightness of an illuminated image.
Figure 4:
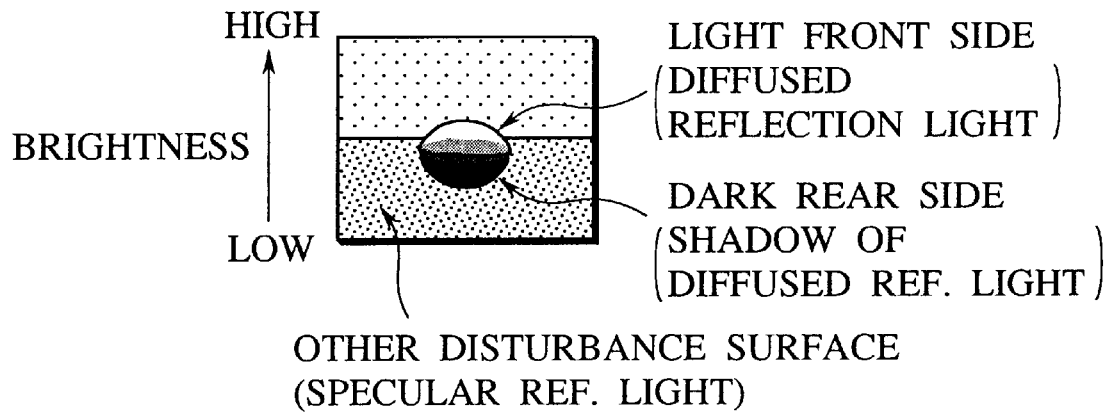
FIG. 4 is a view showing the illuminated image obtained by the surface inspecting apparatus of the present invention.

Now, providing that the emitting angle (90°−α) of the illumination light is less than 10 degrees (see FIG. 3), then the image of the defect would be obtained with high brightness, as shown in FIG. 4. As shown in FIG. 3, this tendency of high brightness becomes to be remarkable as the emitting angle is decreased.

Figure 5:
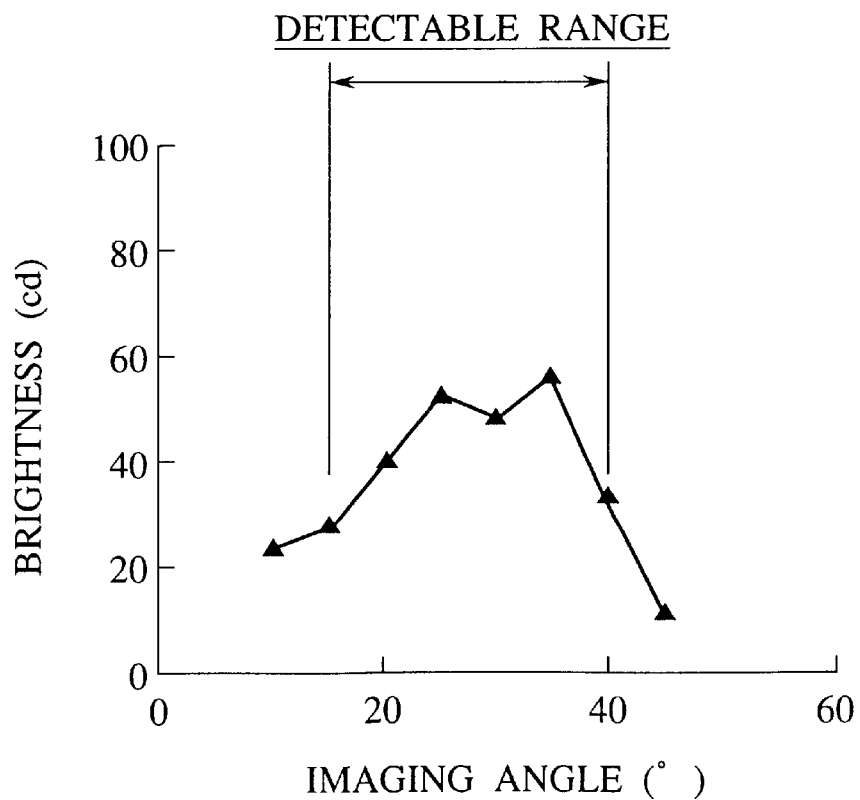
FIG. 5 is a graph showing a relationship between an imaging angle of an imaging unit and the brightness of the illuminated image.

Further, although the CCD cameras 12, 14 respectively exhibit the highest sensitivity when the imaging angle is equal to an angle to capture the diffused reflection light reflected at the reflection angle β, i.e. (90°−β) of the picture pickup (imaging) angle, it should be noted that the reflection light has a distribution in angle and further, the gentler the inclination angle θ of the defect becomes, the closer the specular reflection angle α approaches the diffused reflection angle β. Therefore, it is preferable to keep the imaging angle θc away from the reflection angle α of the diffused reflection light and also bring the imaging angle θc near the reflection angle β of the diffused reflection light, as possible. For example, as shown in FIG. 5, when the imaging angle θc is established in the range from 15 to 40 degrees, it is possible to catch the defects or the like with high brightness.

Note, since the CCD cameras 12, 14 are positioned to the inspected surface of the body panel 10 in angle, there is a possibility that the image of the defect is out of focus at its front and rear ends because of the narrowed depth of field. In such a case, it is necessary to enhance the luminance of the linear light sources 11, 13 for their intense irradiation and also stop the lenses of the cameras 12, 14 down for the increased depth of field as possible. Then, even if the defect has a gentle inclination angle θ and is extremely low in height, it would be possible to catch the defect only as a part with high brightness.

As shown in FIG. 1, the surface inspecting apparatus further comprises the following elements:
- a panel-sort input unit 16 for inputting the sort of the body panel 10, as an inspected surface sort input unit;
- a panel surface information specifying section 17 which, on the basis of the positional information of the body panel 10 obtained by the panel position detecting sensor 15 and the panel-sort information inputted to the panel-sort input unit 16, specifies curved configuration and inclination angle of the inspected surface of the body panel 10 in a position corresponding to the above positional and panel-sort information, as an inspected surface information specifying unit; and
- an emitting/imaging angle and position control section 18 which performs both parts of an emitting angle and position control unit for controlling the height and emitting angle of each linear light source 11, 13 and an imaging angle and position control unit for controlling the pickup angle and height of each CCD camera 12, 14, on the basis of the angular information of the panel surface obtained by the panel surface information specifying section 17 and the positional information of the body panel 10 obtained by the panel position detecting sensor 15.

In operation, the respective adjusting mechanisms for the light sources 11, 13 and the cameras 12, 14 are controlled on the basis of control signals generated from the emitting/imaging angle and position control section 18, so that the emitting angles of the linear light sources 11, 13 and the imaging angles of the CCD cameras 12, 14 can be adjusted so as to be respective predetermined values with respect to the inspected surface of the body panel 10.

Furthermore, the surface inspecting apparatus includes a front-to-back illuminating and imaging switching section 19 which carries out the switching in operation between a couple of the linear light source 11 illuminating the front side of the body panel 10 and the accompanying CCD camera 12 and another couple of the linear light source 13 illuminating the rear side of the body panel 10 and the accompanying CCD camera 14, on the ground of the positional information of the body panel 10 in the transporting direction (L) obtained by the panel position detecting sensor 15 and the angular information of the panel surface obtained by the panel surface information specifying section 17.

Inputted into the front-to-back illuminating and imaging switching section 19 is a detecting signal of a detecting unit 67 which detects the position and moving speed of the body panel 10 under transportation and which will be described later. The illuminating and imaging switching section 19 judges the timing of switching on the basis of the detecting signal of the detecting unit 67 and generates the output signal.

That is, based on the output signals from the front-to-back illuminating and imaging switching section 19, an illuminating power switch 20 and an image input switch 21 are operated in the vicinity of a boundary between the inspectable ranges, whereby the illuminated (light-receiving) image of the front side of the body panel 10 can be obtained by the linear light source 11 and the CCD camera 12, while the illuminated image of the rear side of the body panel 10 can be obtained by the linear light source 13 and the CCD camera 14.

Figure 6:
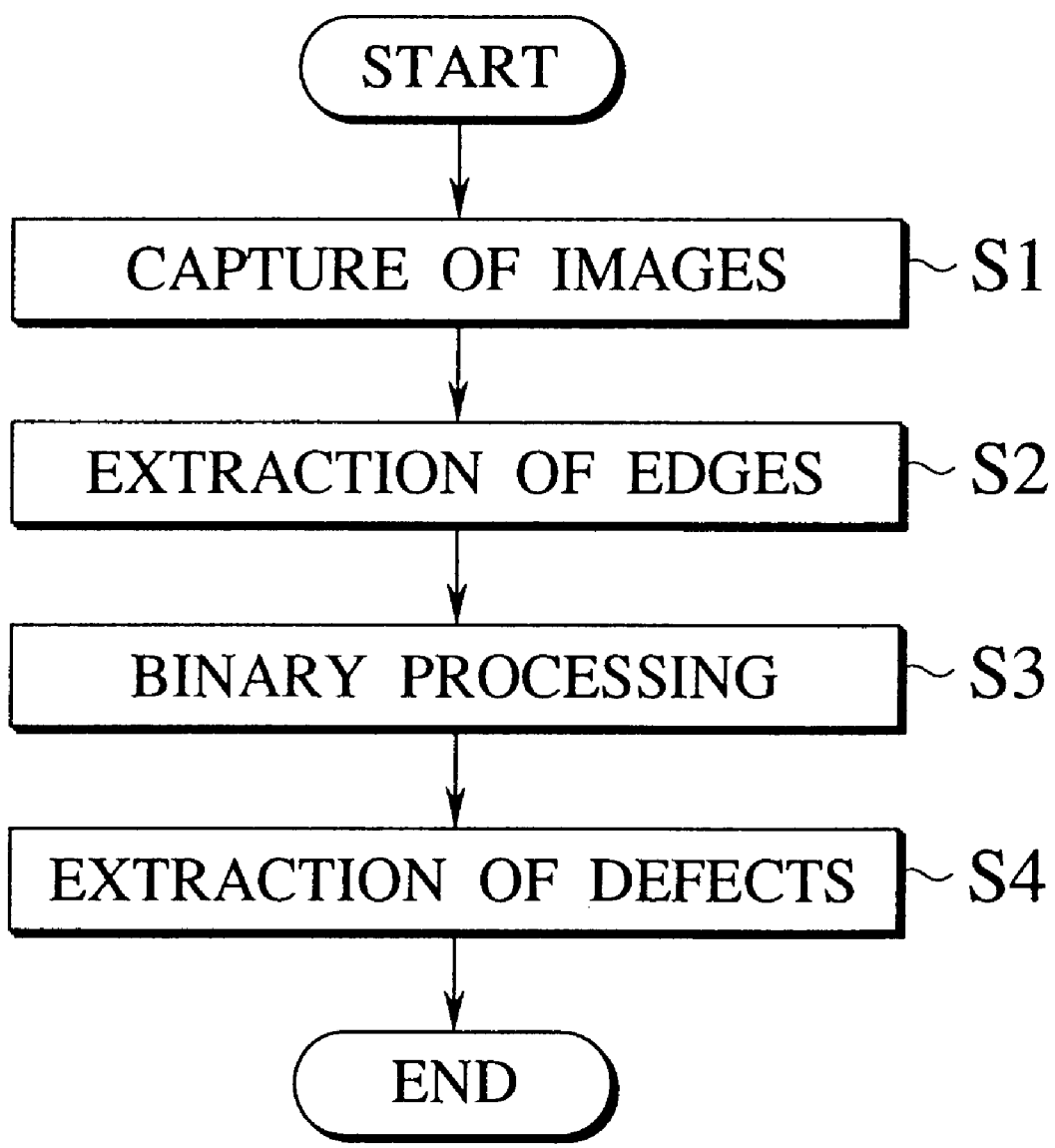
FIG. 6 is a flow chart showing processes executed by an inspecting unit of the surface inspecting apparatus of the invention.

Then, as shown in FIG. 6, the illuminated image captured in the above way is subjected to a picture processing consisting of an edge extracting process (step S2), a binary process (step S3) and a defect extracting process (step S4) etc. by an image (picture) processing section 22 and thereafter, displayed on a display 23.

The operations of the panel surface information specifying section 17, the emitting/imaging angle and position control section 18 and the front-to-back illuminating and imaging switching section 19 are performed by a host computer 24. Further constituted by the image input switch 21, the picture processing section 22 and the display 23 etc. is an inspecting process unit 25 which detects the defects existing on the inspected surface on the basis of the emitted image obtained by the imaging units (cameras) and generates the detecting information.

When it is executed to control the emitting angles of the linear light sources 11, 13 and the imaging angles of the CCD cameras 12, 14 in the above-constructed surface inspecting apparatus, the position of the body panel 10, which is being transported in the direction of arrow L by the a belt conveyer or the like, is firstly detected by the panel position detecting sensor 15 at first. Then, while tracing the panel surface from the front end in sequence on the basis of the above positional information of the body panel 10 and the panel-sort information previously inputted from the panel-sort input unit 16, the emitting angle and the imaging angle etc. corresponding to the respective positions of the body panel 10 are calculated by the host computer 24 and thereafter, the control signals are outputted to the adjusting mechanism thereby to control the emitting angles and heights of the linear light sources 11, 13 and the imaging angle and heights of the CCD cameras 12, 14 for every positions of the panel surface.

Figure 7:
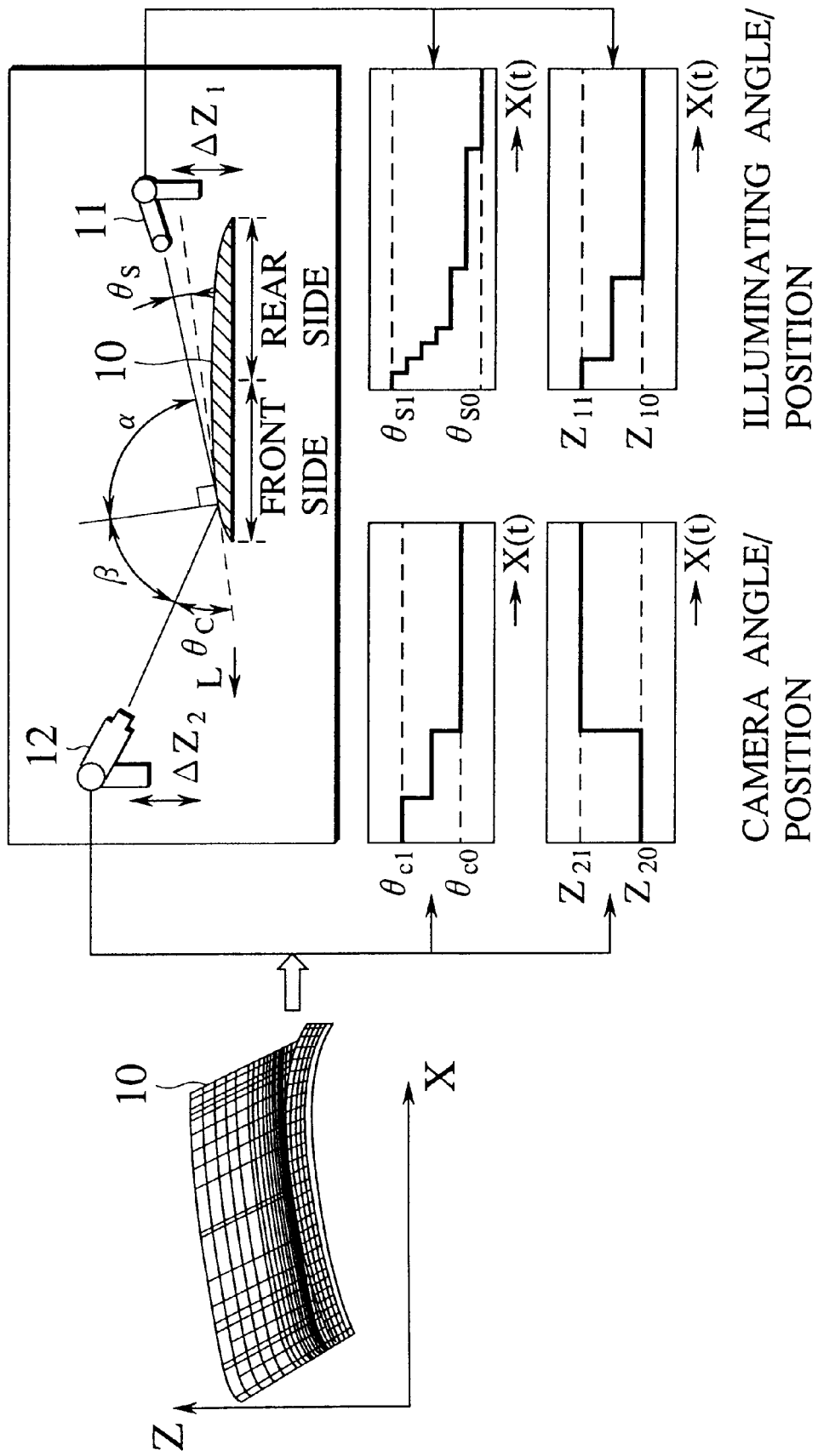
FIG. 7 is an explanatory diagram showing various forms to control respective angles and heights of the illuminating unit and the imaging unit.

In detail, as shown in FIG. 7, all of the imaging angle $\theta c$, the imaging height $\Delta Z_2$, the emitting angle $\theta s$, the imaging height $\Delta Z_1$ are controlled so as to change in a step manner. The reason why the invention adopts such a controlling method is that both of the emitting angles of the linear light sources 11, 13 and the imaging angles of the CCD cameras 12, 14 have some latitude in inspectable angles and therefore, the respective angles have only to be controlled so as not to be out of the inspectable angles. Again, the reason of the above adoption is also that since the linear light sources 11, 13 have some allowance, i.e. orientation in height, it only has to control the respective heights so that the linear light sources can illuminate the inspected surface in accordance with the heights changing due to the curved surface of the body panel 10. Note, in the modification, the successive control of the angles $\theta c$, $\theta s$ and the heights $\Delta Z_2$, $\Delta Z_1$ along the surface of the body panel 10 would cause the inspection to be more appropriate.

Figure 8:
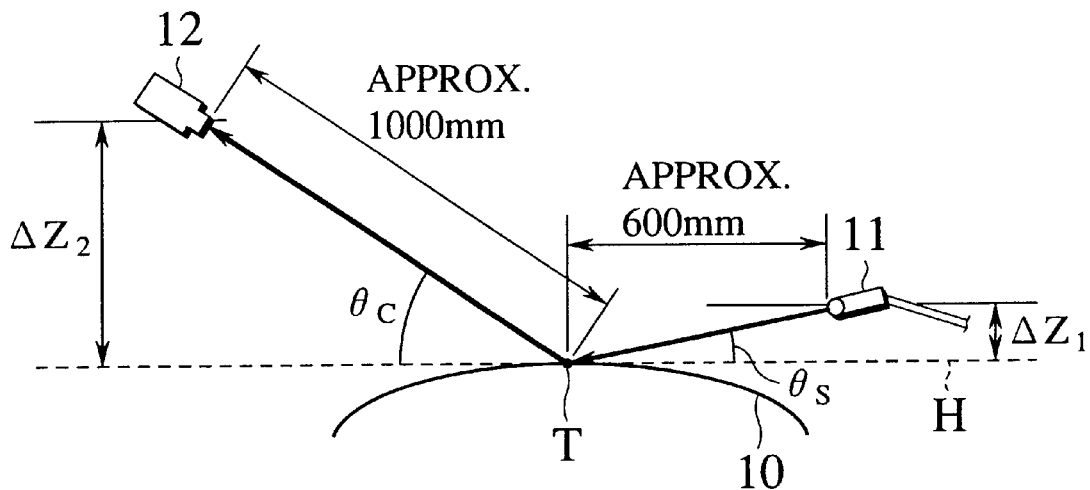
FIG. 8 is a diagram for definition of the heights of the illuminating unit and the imaging unit of the surface inspecting apparatus of the invention.

Next, we give a definition of the emitting height $\Delta Z_1$ and the imaging height $\Delta Z_2$ with reference to FIG. 8. Now, a tangential line at the highest point T of the body panel 10 in the direction (height direction) Z coincides with a horizontal line H. A height of the linear light source 11 on the basis of the horizontal line H is defined as $\Delta Z_1$, while another height of the CCD camera 12 on the basis of the horizontal line H is defined as $\Delta Z_2$. An angle between the tangential line of the body panel 10 and the illumination light emitted from the linear light source 11 is defined as the emitting angle $\theta s$, while another angle between the tangential line of the body panel 10 and the diffused reflection light entering the CCD camera 12 is defined as the imaging angle $\theta c$. In a preferred embodiment, a distance from the highest point T to the linear light source 11 is established to approx. 600 mm, while a distance from the highest point to the CCD camera 12 is done to approx. 1,000 mm.

Figure 9A:
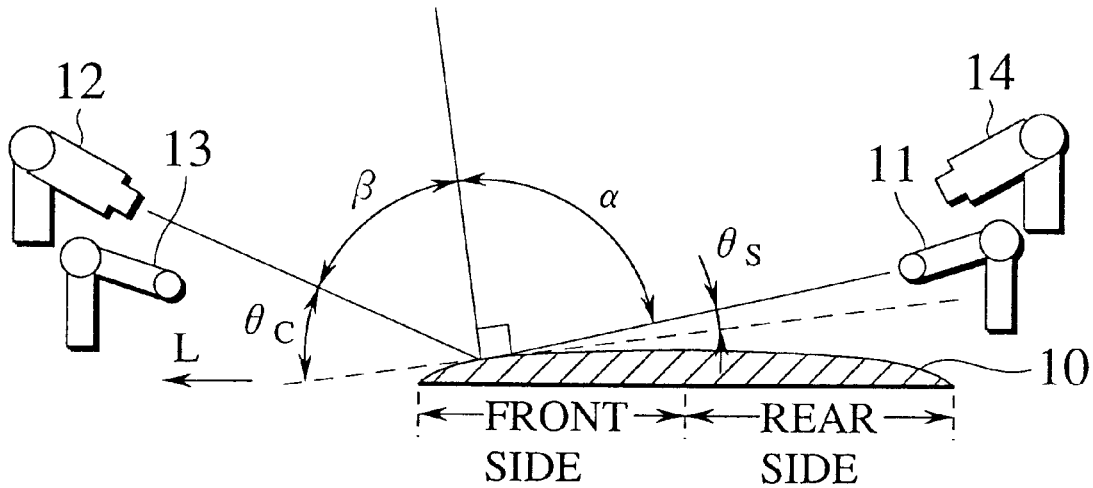
FIGS. 9A and 9B are diagrams showing illuminating and imaging conditions by the illuminating units and the imaging units where
Figure 9B:
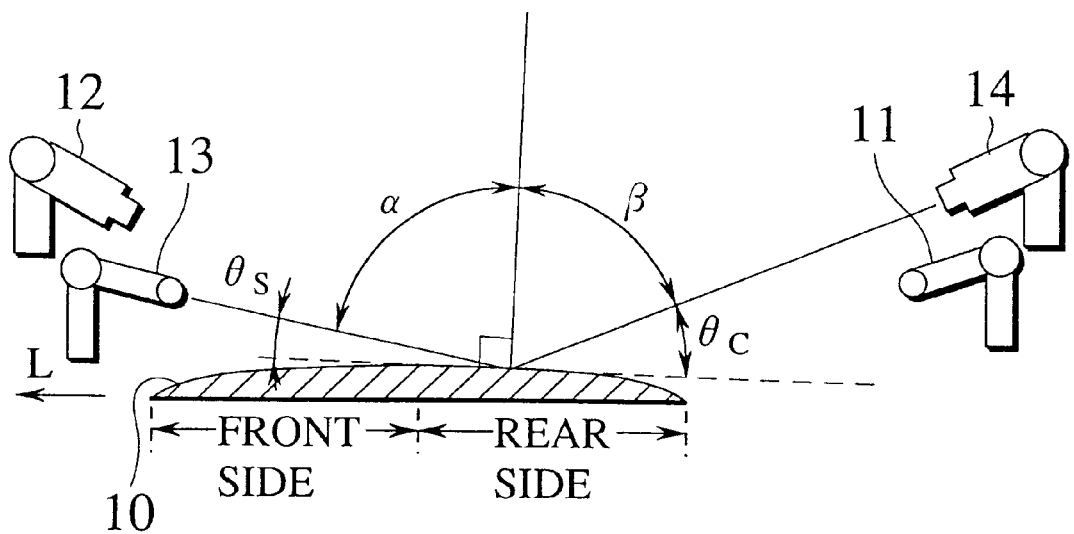

We now describe a method of switching in illuminating and picking-up between the front side and the rear side of the convex body panel 10, with reference to FIGS. 9A and 9B. At first, it is carried out to irradiate the front side of the body panel 10 by the linear light source 11 and also take a picture of the front side by the CCD camera 12, as shown in FIG. 9A. Then, with the transportation of the body panel 10 in the direction of arrow L, when the emitted area reaches the vicinity of the highest point where the inclined direction of the panel surface is reversed, the switching of illuminating and imaging is executed between one couple of the light source and the CCD camera and the other couple. That is, as shown in FIG. 9B, the rear side of the body panel 10 is illuminated by the linear light source 13 and sequent picked up by the CCD camera 14.

Consequently, it is possible to detect the gentle irregularities, projections etc. on the whole surface of the body panel 10 with high accuracy and reliability while transporting the body panel 10.

Figure 10:
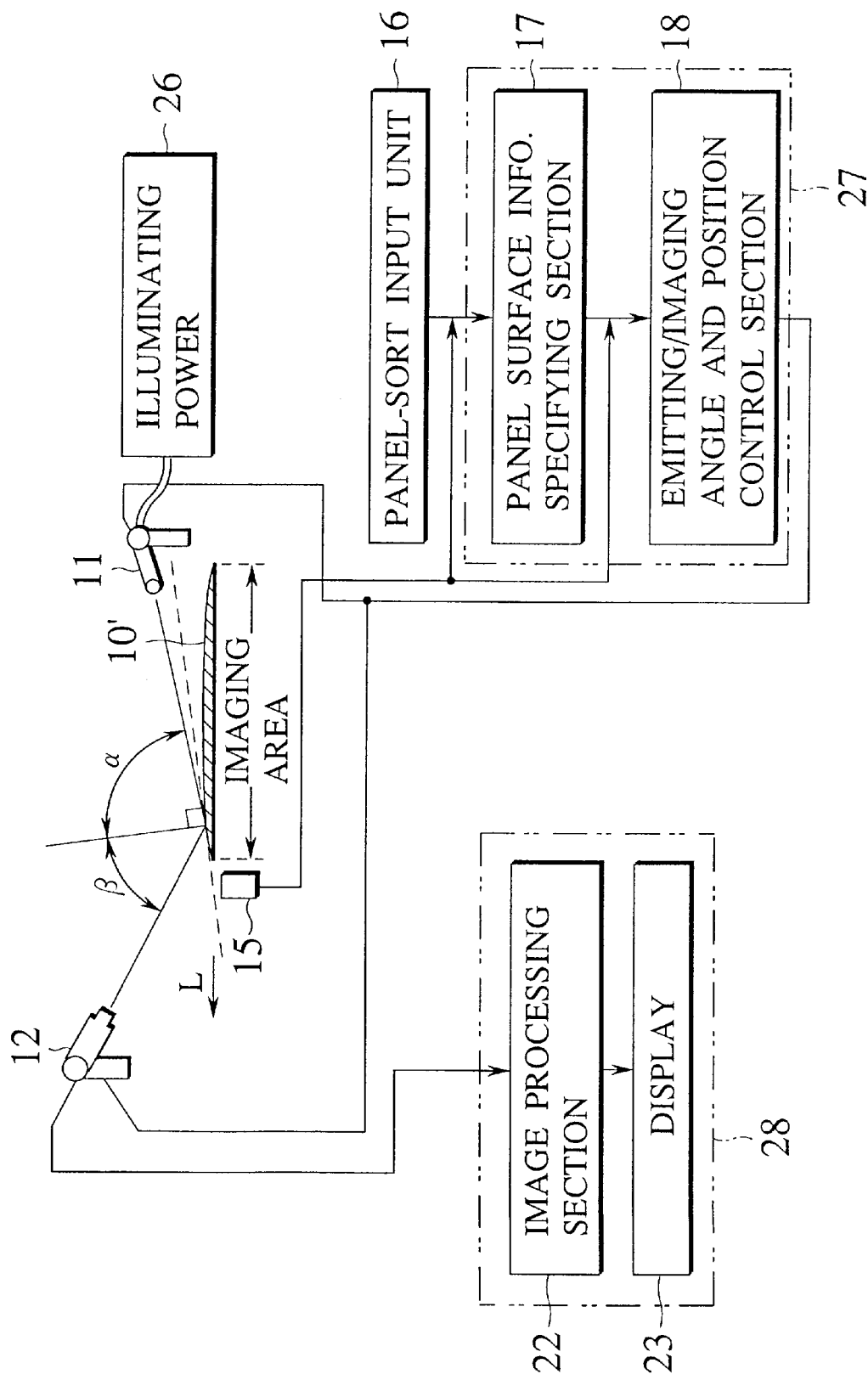
FIG. 10 is a schematic view showing a constitution of the surface inspecting apparatus in accordance with a second embodiment of the present invention.

Although two couples of the linear light sources 11, 13 and the CCD cameras 12, 14 are used in the above-mentioned embodiment, as shown in FIG. 10, it is possible to inspect the whole area of a body panel 10' by the only linear light source 11 and the only CCD camera 12 when the body panel 10' has an inclination angle allowing the emitting angle $\theta s$ to be established less than 10 degrees over the whole surface area of the body panel 10 by the single illuminating unit.

In such a case, the surface inspecting apparatus has only to be equipped with the panel position detecting sensor 15, the panel-sort input unit 16, the panel surface information specifying section 17, the emitting/imaging angle and position control section 18, the picture processing section 22, the display 23 and an illumination power source 26, in addition to one couple of the linear light source 11 and the CCD camera 12, while removing the afore-mentioned front-to-back illuminating and imaging switching section 19 or the like.

Note, in the surface inspecting apparatus provided with the above constitution, a host computer 27 performs respective parts of the panel surface information specifying section 17 and the emitting/imaging angle, while both of the picture processing section 22 and the display 23 etc. constitute an inspection unit 28.

Figure 11:
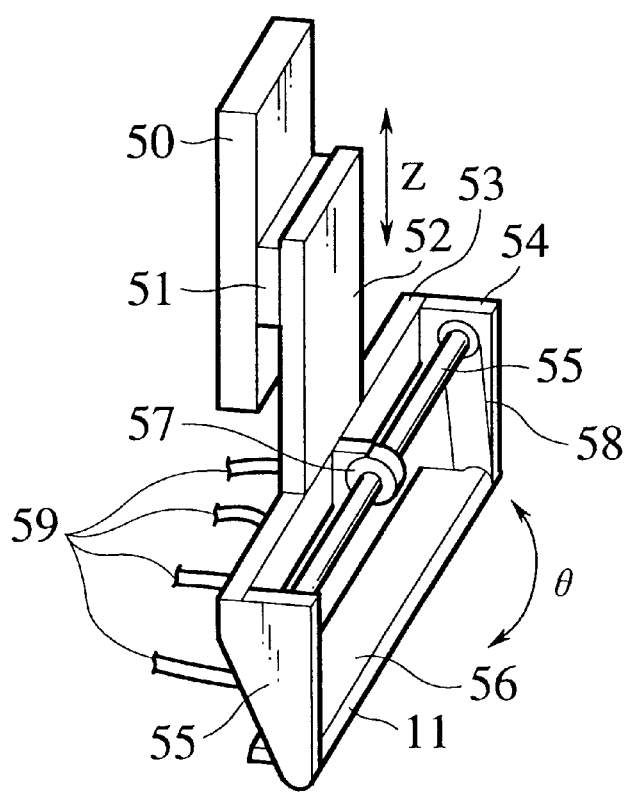
FIG. 11 is a diagram showing an example of an adjusting mechanism of the illuminating unit of the surface inspecting apparatus of the invention.

Now, referring to FIG. 11, we describe an example of an adjusting mechanism controlled by the emitting/imaging angle and position control section 18. This is a definite sample of an angular position control apparatus for the linear light source 11. In FIG. 11, a retainer 52 is mounted on a fixed part 50 through the intermediary of a driving mechanism 51 consisting of a motor and a ball screw. The retainer 52 is driven by the driving mechanism 51 up and down (the direction Z), whereby the adjustment in the direction Z can be effected. A pair of side jigs 54, 54 are secured on both sides of a transverse beam 53 attached on a lower end of the retainer 52. Rotatably supported by the side jigs 54, 54 are a shaft 55 and a light guide 56 both of which extend in a transverse direction. The shaft 55 is rotated by a rotating mechanism 57, so that the rotation of the shaft 55 is transmitted to the light guide 56 via a timing belt 58 for the adjustment of illumination angle. Optical fibers 59 for the illumination light are connected to the backside of the light guide 56, so that the illumination light is emitted from the linear light source 11 on the light guide 56 forward (to the right side of FIG. 11).

Figure 12:
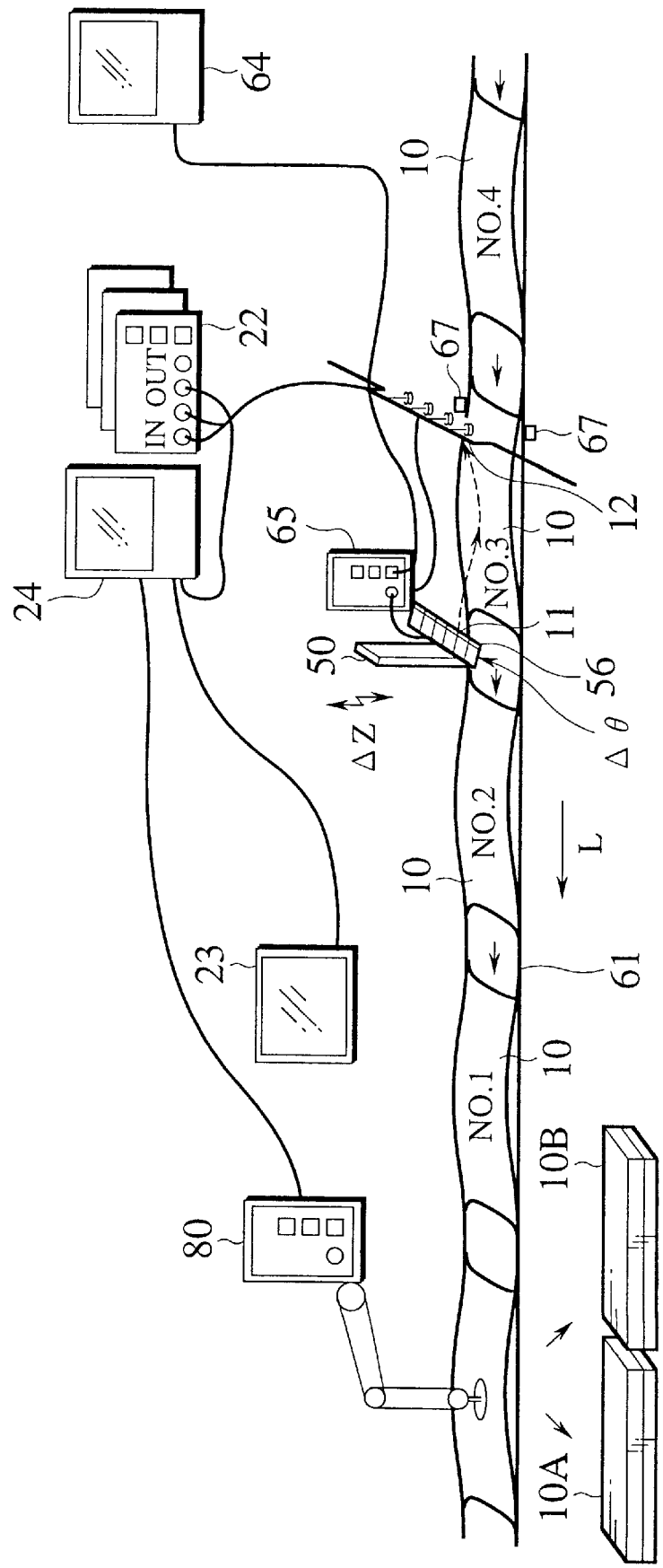
FIG. 12 is a diagram showing an example of a detecting line to inspect a body panel, in which the surface inspecting apparatus of the invention is installed.

FIG. 12 shows an example of a defect inspecting line for the body panels 10. The body panels 10 as objects to be inspected are transported on a belt conveyer 61 from the right to the left of FIG. 12. Above the belt conveyer 61, the linear light source 11 and the accompanying CCD camera 12 are arranged to oppose each other. The CCD camera 12 is also provided with an adjusting mechanism similar to the above-mentioned adjusting mechanism for the linear light source 11. The adjusting mechanism are controlled by the control signals outputted from the emitting/imaging angle and position control section 18 in the host computer 24 through the intermediary of a binary controlled computer 64 and a driver 65. The received image on the CCD camera 12 is displayed on the display 23 after being picked up by the picture processing unit 22 for picture-processing. The detecting units 67 are arranged in the vicinity of the belt conveyer 61, for detecting the position and moving speed of the body panel 10. The signals from the detecting units 67 are inputted into the illuminating and imaging switching section 19, so that the switching in operation is carried out between the plural linear light sources 11, and also done between the plural CCD cameras 12,. The host computer 24, which judges whether the body panel 10 has a defect or not, controls a panel selecting unit 80 to classify between the "non-repair" panels 10A having no defect and the "repair" panel 10B requiring to be repaired. Note, as to the positional relationship between the linear light source 11 and the CCD camera 12, the relationship shown in FIG. 12 is opposite to that of FIG. 1.

Figure 13:
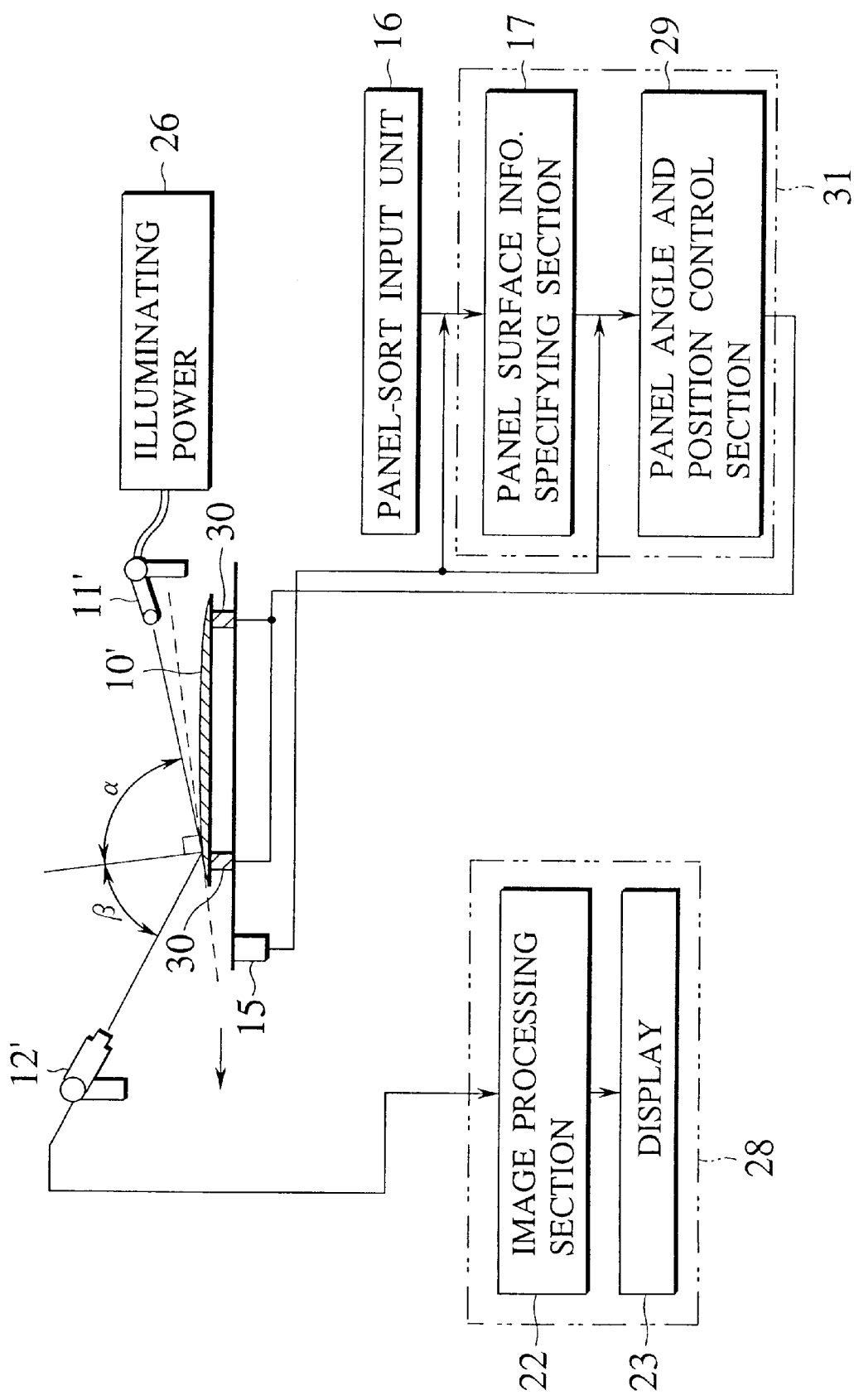
FIG. 13 is a schematic view showing a constitution of the surface inspecting apparatus in accordance with a third embodiment of the present invention.

FIG. 13 show a constitution of the surface inspecting apparatus in accordance with the other (3rd.) embodiment of the present invention. As shown in FIG. 13, the surface inspecting apparatus of this embodiment includes:

a linear light source 11' fixed obliquely upward the body panel 10 on one side at a predetermined height and a predetermined emitting angle;

a CCD camera 12' fixed obliquely upward the body panel 10 on the other side at a predetermined height and a predetermined imaging angle;

the panel position detecting sensor 15 for detecting a position of the body panel 10 in the transporting direction (L) during the transportation by the belt conveyer 61 (FIG. 12) or the like;

an illuminating power 26;

a height adjusting mechanism 30 arranged on the belt conveyer 61 to support the body panel 10 and adjust a height of the body panel 10 at its supported portions;

the afore-mentioned panel-sort input unit 16 for inputting the sort of the body panel 10;

a panel surface information specifying section 17 which, on the basis of the positional information of the body panel 10 obtained by the panel position detecting sensor 15 and the panel-sort information inputted to the panel-sort input unit 16, specifies the curved configuration and the inclination angle of the inspected surface of the body panel 10 in the position corresponding to the above positional and panel-sort information; and a panel angle and position control section 29 which controls the inclination angle and the height of the surface of the body panel 10 on the basis of the angular information of the inspected part obtained by the panel surface information specifying section 17 and the positional information obtained by the panel position detecting sensor 15, that is, serving as a surface angle and position control section of the invention. In operation, respective height adjusting mechanisms 30 are controlled by the output signals from the panel angle and position control section 29 thereby to adjust the inclination angle etc. of the surface to be inspected of the body panel 10 to be the respective predetermined values.

Then, as shown in FIG. 6, the illuminated image obtained by the CCD camera 12' is processed by the image processing section 22 and subsequently displayed on the display 23.

Note, in the surface inspecting apparatus provided with the above constitution, a host computer 31 performs respective parts of the panel surface information specifying section 17 and the panel angle and position control section 29, while both of the picture processing section 22 and the display 23 etc. constitute the inspection unit 28.

When it is required to control the inclination angle and height of the body panel 10 relative to a predetermined reference surface in the above-constructed surface inspecting apparatus, a position of the body panel 10, which is transported in the direction of arrow L by the belt conveyer 61 or the like, is detected by the panel position detecting sensor 15 at first. Next, on the basis of the above positional information of the body panel 10 and the panel-sort information previously inputted from the panel-sort input unit 16, it is executed to trace the panel surface from the front end in sequence, while the inclination angle of the body panel 10 relative to the reference surface, for example the horizontal surface is calculated by the host computer 31. Thereafter, the control signals are outputted to the adjusting mechanisms 30 thereby to realize, for example horizontal inspected area on the body panel 10 usually.

Figure 14:
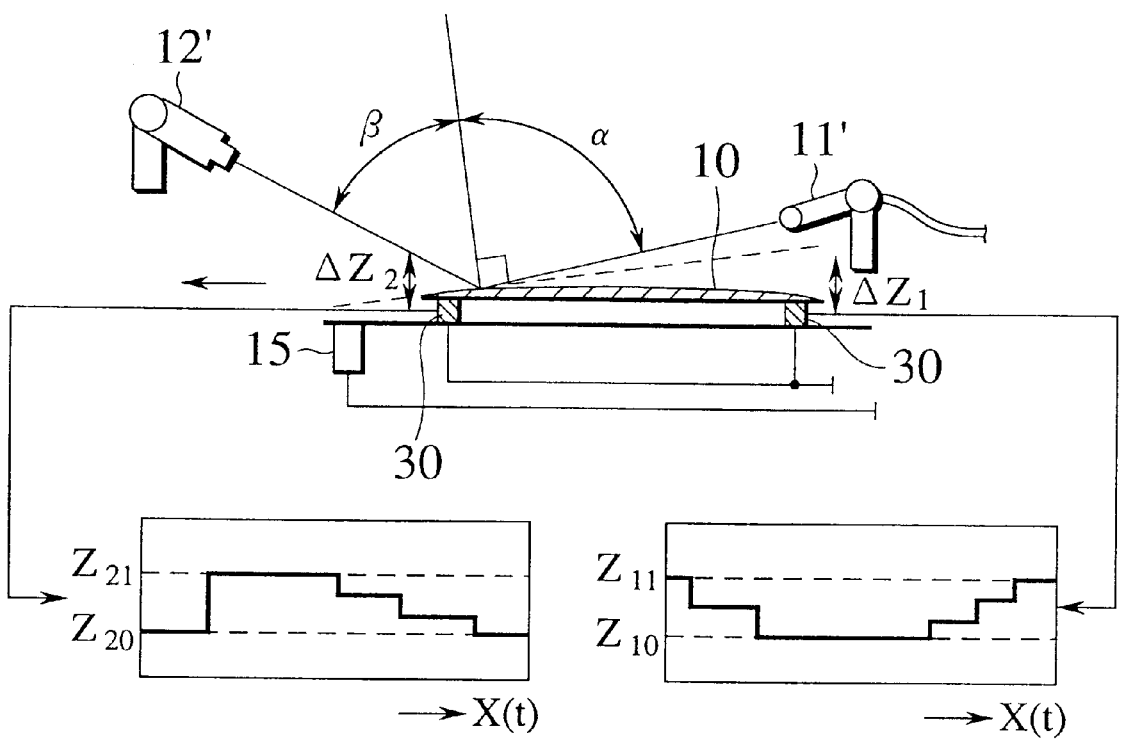
FIG. 14 is an explanatory diagram showing a form to control an inclination angle and a height of the surface in the surface inspecting apparatus of FIG. 13.

In detail, as shown in FIG. 14, both angles of the body panel 10 relative to the horizontal surface are changed in a step manner. The reason why the invention adopts such a controlling method is that both of the emitting angle of the linear light source 11' and the imaging angle of the CCD cameras 12' have some latitude in inspectable angles and therefore, the respective angles have only to be controlled so as not to be out of the inspectable angles. Note, in the modification, the successive control of the inclination angles along the surface of the body panel 10 would cause the inspection to be more appropriate.

As the other methods of changing the inclination angle and height of the body panel 10 by the above-mentioned height adjusting mechanisms 30, there are a method to drive one of the front-to-rear height adjusting mechanisms 30 while fixing the other mechanism 30, another method of driving both of the mechanisms 30 independently or the like. Further, in order to maintain the inspected portion of the body panel 10 usually and horizontally, it may be adopted to arrange rollers etc. along the curved back surface of the body panel 10 separately from the belt conveyer so that the panel 10 is transported along the rollers etc.

Figure 15:
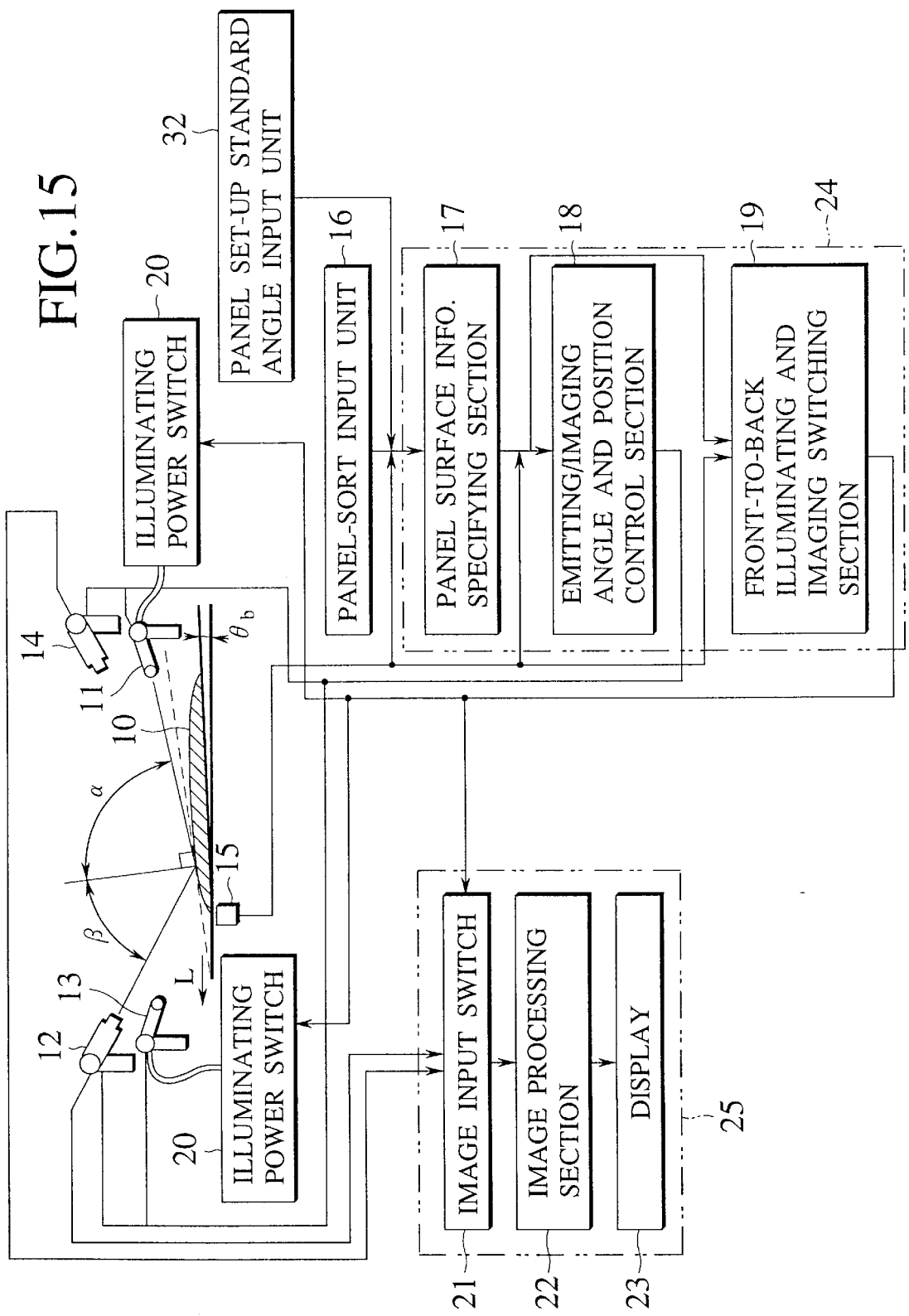
FIG. 15 is a schematic view showing a constitution of the surface inspecting apparatus in accordance with a fourth embodiment of the present invention.
Figure 16:
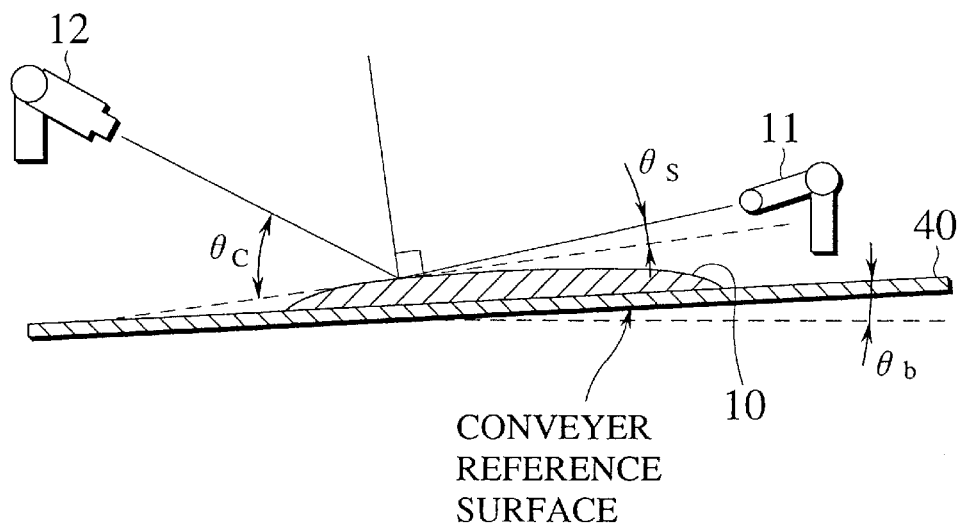
FIG. 16 is an enlarged diagram of a part of the surface inspecting apparatus of FIG. 15.

FIG. 15 is a constitution diagram of the surface inspecting apparatus in accordance with the other (4th.) embodiment of the present invention and FIG. 16 is an enlarged diagram of a part of this surface inspecting apparatus. The surface inspecting apparatus of the embodiment is provide for inspecting the body panel 10 in case of the inclined reference surface of the belt conveyer etc. transporting the panel 10. In addition to the constituents of the surface inspecting apparatus of FIG. 1, a set-up panel standard angle input unit 32 as the setting angle inputting unit is provided to input a set angle of inclination during transporting the body panel 10, namely, an inclination angle θb of the standard surface of the belt conveyer 40 relative to a predetermined reference surface, for example the horizontal plane. Therefore, on the basis of the positional information of the body panel 10 obtained by the panel position detecting sensor 15, the panel-sort information inputted to the panel-sort input unit 16 and the inclined angle information of the standard surface of the belt conveyer 40 inputted into the set-up panel standard angle input unit 32, the panel surface information specifying section 17 of the surface inspecting apparatus is adapted, so as to specify the curved configuration and inclination angle of the inspected surface of the body panel 10 in a position corresponding to the above-mentioned informations.

In operation, on the basis of the angle information about the panel surface brought by the panel surface information specifying section 17 and the positional information owing to the panel position detecting sensor 15, the respective adjusting mechanisms are controlled while correcting the inclination angle about the standard surface of the belt conveyer, so that the angles and heights of the linear light sources 11, 13 and the CCD cameras 12, 14 can be adjusted so as to be respective predetermined values.

Owing to the above-mentioned constitution of the surface inspecting apparatus, it is possible to detect the gentle irregularities and projections etc. with high accuracy and reliability, even if the standard surface (mount surface) of the belt conveyer 40 (FIG. 16) is inclined.

In common with the above-mentioned embodiments, the linear light sources 11, 11', 13 may be constituted by illuminating units each of which collects light, which has been introduced from a luminance source (e.g. a halogen lamp, an intensive metal halide lamp, a more intensive xenon metal halide lamp) through the intermediary of an optical fiber or directly, in the form of a line by means of a lens. Further, as the imaging units, they are not limited to the CCD cameras shown in the embodiment, so that other various imaging units are applicable to the imaging units, of course.

FIGS. 17 to 20 show the other (5th.) embodiment of the invention.

Figure 17:
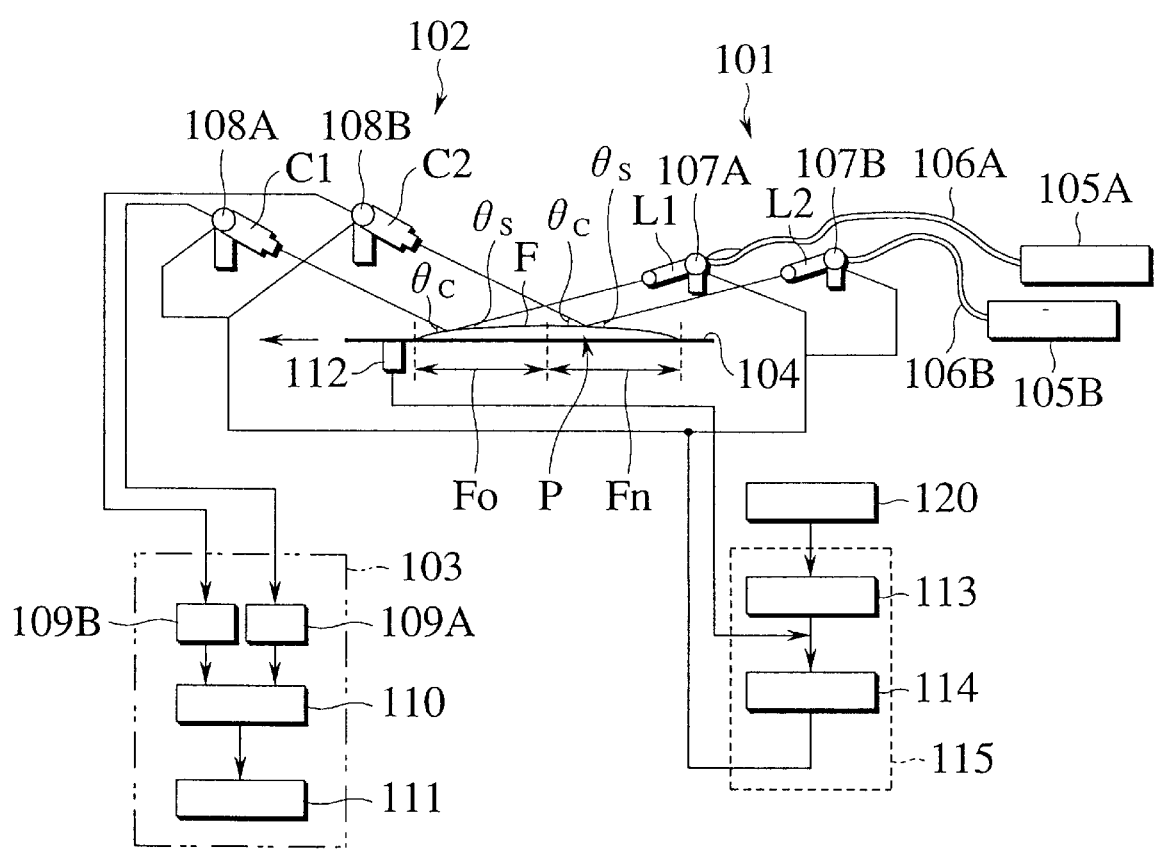
FIG. 17 is a schematic view showing a constitution of a surface inspecting apparatus in accordance with a fifth embodiment of the present invention.

The surface inspecting apparatus shown in FIG. 17 includes an illuminating device 101 for emitting light at the emitting angle θs inclined to an inspected surface F of a body panel P, an image input device 102 opposed to the illuminating device 101 to take a picture of the surface F at the imaging angle θc larger than the emitting angle θs, and an image processing unit 103 for extracting surface defects from the image captured by the image input device 102.

The body panel P, for example a door panel, has a curved outer surface corresponding to the surface F to be inspected. Under condition of turning the surface F upward, the body panel P is transported by a conveyer unit 104 to one direction (left hand of FIG. 17) at a constant speed. As the conveyer unit 104, a panel conveyer in a press line may be adopted.

The illuminating device 101 comprises first and second illuminating units L1 and L2 corresponding to the linear light sources (11, 11', 13) of the previous embodiments, two luminous sources 105A, 105B and optical fibers 106A, 106B for feeding light from the luminous sources 105A, 105B to the illuminating units L1, L2, respectively. Each of the illuminating units L1, L2 is provided with an optical system for emitting the light collected in a line manner. The illuminating units L1, L2 are respectively supported by driving mechanisms 107A, 107B allowing each emitting angle θs to be adjusted and having motors serving as the driving source. As each luminous source 105A, 105B, any one of the halogen lamp, the metal halide lamp and the xenon metal halide lamp may be used, for example.

In the illuminating device 101, the illuminating units L1, L2 are arranged in series on the upstream side of the transporting direction due to the conveyer unit 104, providing first and second lighting positions arranged in series along the moving direction of the surface F to be inspected 5. Each of the illuminating units L1, L2 arranged in the above way does emit the light toward the surface F at small emitting angle θs close to the level.

Figure 20:
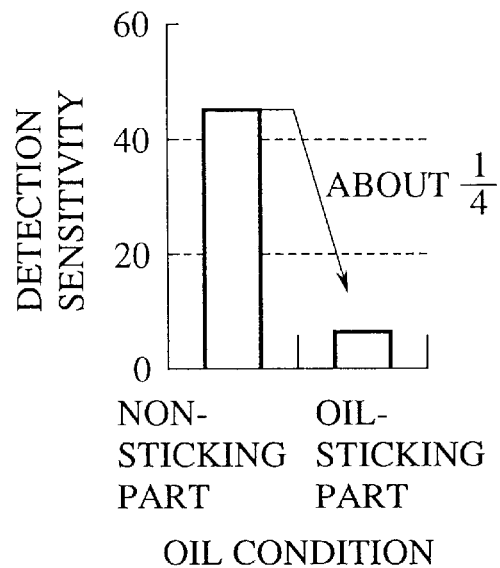
FIG. 20 is a graph showing detecting sensitivity of an oil-sticking portion and a non-sticking portion on the surface to be inspected.

It is general that the body panel P after press-forming has oil such as anticorrosive oil, cleaning oil etc. sticking on the surface F and therefore, it is muddled up with oil-sticking portions Fo and non-sticking portions Fn. Note, for the sake of convenience, we assume that the left portion of the surface F of FIG. 1 corresponds to the oil-sticking portion Fo while the right portion of the surface F does to the non-sticking portion Fn. Further, since the reflectivity of the oil-sticking portion Fo is smaller than that of the non-sticking portion Fn, the detection sensitivity of the image processing unit for the oil-sticking portion Fo is about one-fourth of that for the non-sticking portion Fn, as shown in FIG. 20. This sensitivity for detection can be changed by adjusting the light quantity of the illuminating device 101 or the image input device 102, i.e. controlling the quantity of emitted or received light.

Therefore, according to the embodiment, the light value of the first emitting unit L1 is established to be large corresponding to the small reflectivity of the oil-sticking portion Fo, while the light value of the second emitting unit L2 is established to be small corresponding to the large reflectivity of the non-sticking portion Fn.

The image input device 102 includes first and second cameras C1, C2 as imaging units. The cameras C1, C2, which may be CCD cameras, are supported by driving mechanisms 108A, 108B each allowing the imaging angle θc against the surface F to be adjusted and each having a motor serving as the driving source.

In the image input 102, the first and second cameras C1, C2 are arranged in series on the downstream side of the transporting direction due to the conveyer unit 104, providing first and second imaging (pickup) positions arranged in series along the moving direction of the surface F to be inspected 5. Further, the first and second cameras C1, C2 are arranged so that the first and second imaging positions coincide with the first and second lighting positions, respectively. In operation, each of the first and second cameras C1, C2 take a picture of the surface F at the imaging angle θc larger than the emitting angle θs.

The image processing unit 103 comprises first and second processing sections 109A, 109B into which the respective images on the first and second cameras C1, C2 are inputted, an image composing section 110 for composing defect images obtained by both processing section 109A, 109B and a display 111 for displaying the composite image. Note, a detailed image processing executed in the image processing unit 103 will be described later, together with a description about an operation of the surface inspecting apparatus.

The surface inspecting apparatus further includes a position detecting unit 112 for detecting the surface F moved by the conveying unit 104, a profile output section 113 for outputting information about the profile of the surface F and a drive control section 114 for controlling the directions of the illuminating device 101 and the image input device 102 on the basis of the signals from the position detecting unit 112 and the profile output unit 113.

The position detecting unit 112, which is constituted by a switch or a sensor, is disposed on a stationary part relative to the conveying unit 104, for detecting the surface F of the body panel P entering into a detection area. Based on the detecting signal from the position detecting unit 112 and the transporting speed of the conveying unit 104, it is possible to detect the position of the moving surface F and the imaging positions of the cameras C1, C2 of the image input device 102.

The profile output section 113 and the drive control section 114 are included in a host computer 115. Inputted into the profile output section 113 is information from a panel-sort output unit 120 which is disposed outside the host computer 115. The information (CAD information) about dimensions etc. of a variety of body panels is stored in the panel-sort output unit 120. The profile output section 113 operates to input the CAD information of the body panel P from the panel-sort output unit 120 in order to calculate the curvature of the surface F to be inspected. Thus, according to the embodiment, on the basis of the signals from the position detecting unit 112 and the profile output section 113, it is possible to detect the profile of the surface at the imaging position successively varying with the movement of the surface F to be inspected.

Inputting the signals from the position detecting unit 112 and the profile output section 113, then the drive control section 114 generates command signals to drive the driving mechanisms 107A, 107B of the illuminating units L1, L2 of the illuminating device 101 and the driving mechanisms 108A, 108B of the respective cameras C1, C2 of the image input device 102, thereby to change the respective directions of the illuminating units L1, L2 and the camera C1, C2 so as to cause the emitting angle θs and the imaging angle θc for the surface F to be fixed usually.

The so-constructed surface inspecting apparatus operates as follows.

While moving the surface F to be inspected to one direction at a constant speed by the conveying unit 4, the surface inspecting apparatus operates to emit the light against the surface F through the illuminating units L1, L2 of the illuminating device 101 at the small emitting angle θs close to the level and also operates to image the surface F through the cameras C1, C2 of the image input device 102 at the intermediate imaging angle θc larger than the small emitting angle θs. Then, since an uneven surface defect on the surface F causes the illumination light to be diffused at the defect, such a surface defect is captured as the diffused light.

Figure 18:
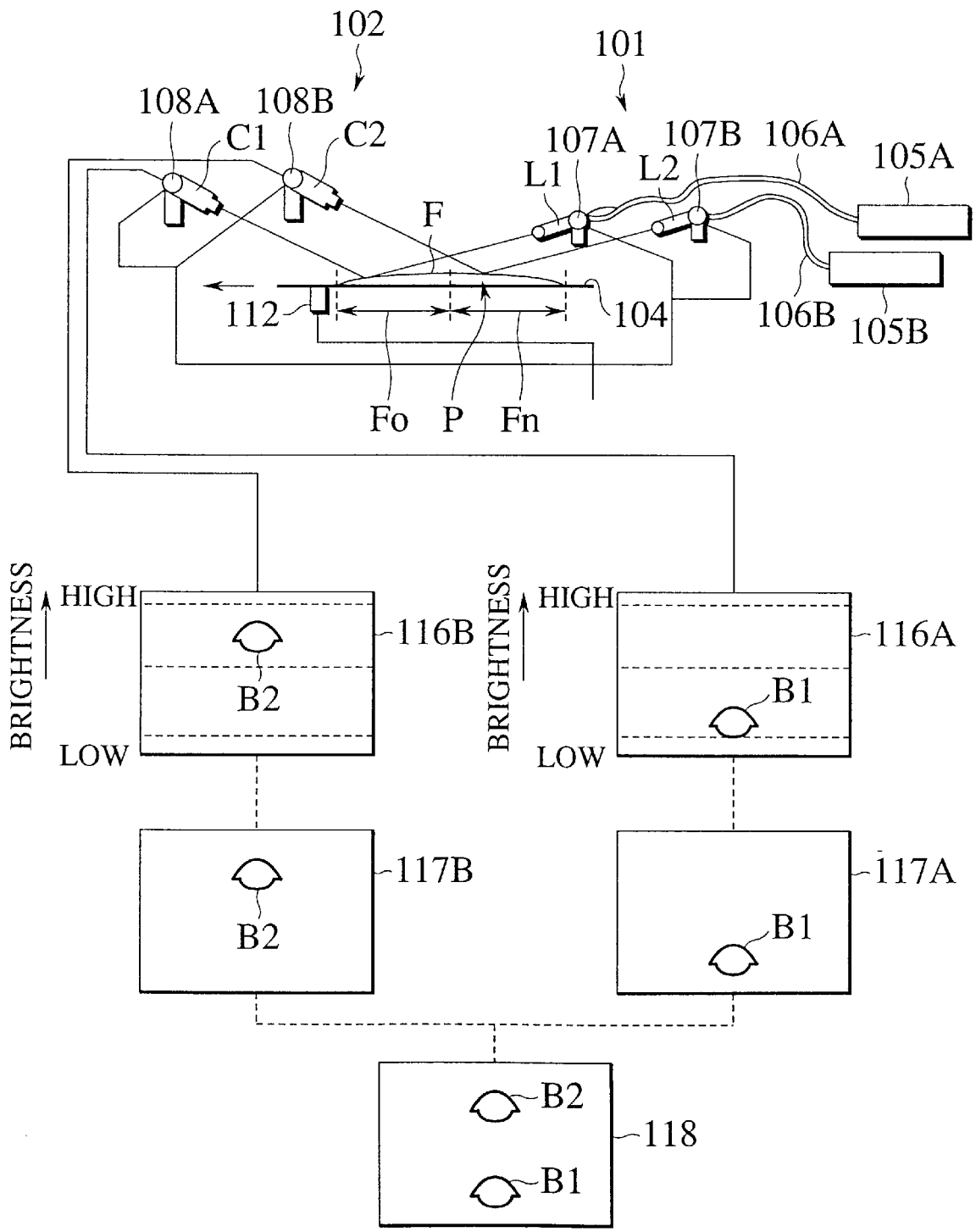
FIG. 18 is an explanation diagram showing various images captured by the surface inspecting apparatus of FIG. 17.

Again, in the surface inspecting apparatus, the light value of the first illuminating unit L1 is established large so as to correspond to the small reflectivity of the oil-sticking portion Fo and it is captured by the first camera C1. Therefore, as shown in FIG. 18, an original picture 116A captured by the first camera C1 has the non-sticking portion Fn imaged unclearly due to its saturated condition and the oil-sticking portion Fo imaged clearly, whereby a surface defect B1 in the oil-sticking portion Fo can be picked up on the image.

While, also in the surface inspecting apparatus, the light value of the second illuminating unit L2 is established small so as to correspond to the large reflectivity of the non-sticking portion Fn and it is captured by the second camera C2. Therefore, in an original picture 116B captured by the second camera C2, the oil-sticking portion Fo is imaged unclearly due to the luck of light value, while the non-sticking portion Fn is imaged clearly, whereby a surface defect B2 in the non-sticking portion Fn can be picked up on the image.

The original image 116A of the oil-sticking portion Fo and the original image 116B of the non-sticking portion Fn captured in the above way are respectively processed in the first and second processing units 109A, 109B.

Figure 19:
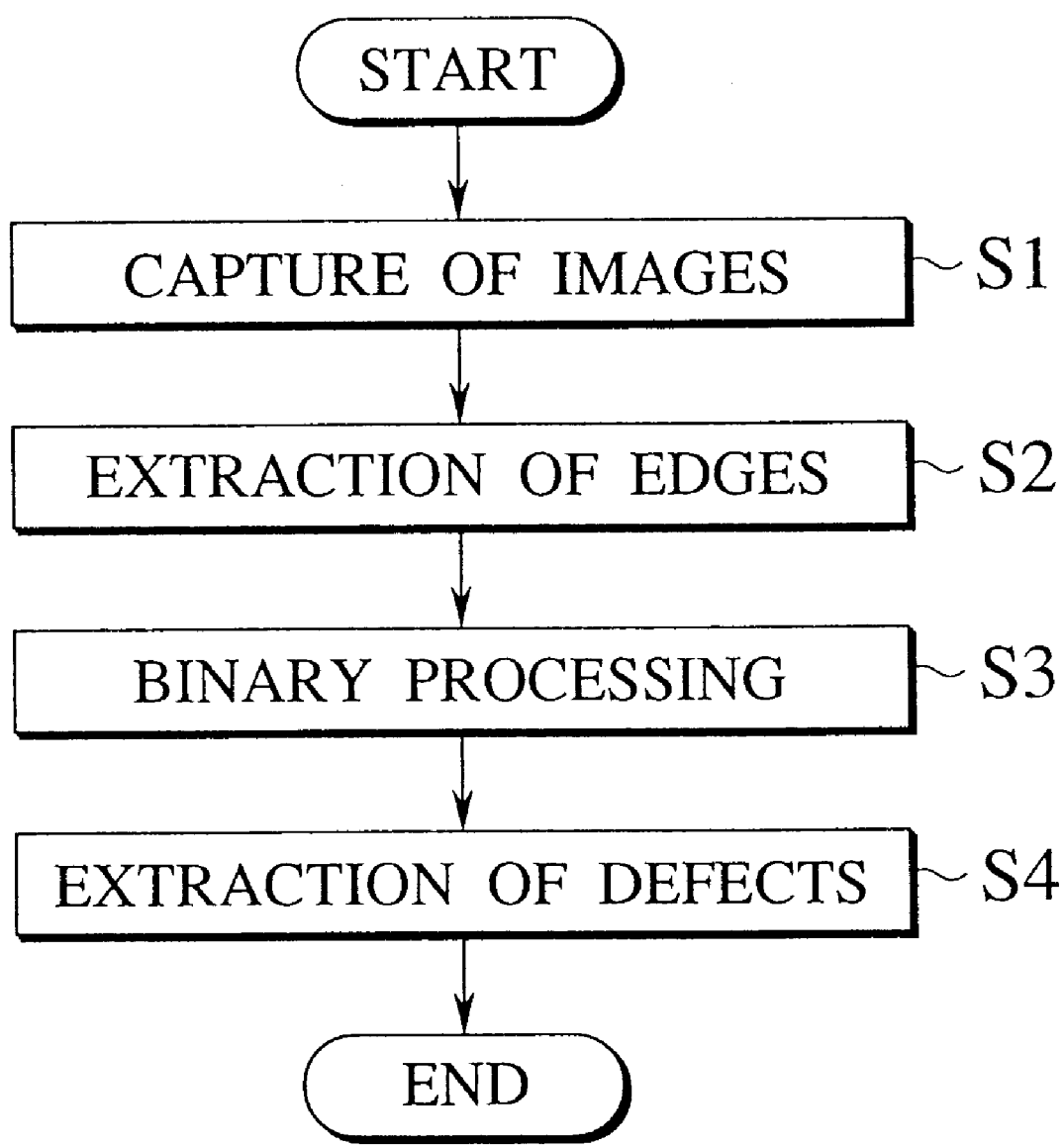
FIG. 19 is a flow chart showing image processing steps executed by an image processing apparatus of the surface inspecting apparatus of FIG. 17.

Regarding the image process carried out in the first and second processing units 109A, 109B, as shown in FIG. 19, it is executed to capture the images at step S1 and thereafter, the extraction of edges is carried out at step S2. In the process of extracting the edges, it is executed to extract the edges of high-luminance portions since the respective surface defects B1, B2 captured as the diffused reflection light exhibit a great luminance on the original images 116A, 116B, in comparison with the surroundings.

Next, the binary processing is executed at step S3. In detail, it is executed beforehand to measure the luminance levels of the surface defects B1, B2 of the oil-sticking portion Fo and the non-sticking portion Fn on the original images and sequentially establish the threshold values suitable to the respective luminance levels. Thus, the original images 116A, 116B are subjected to the binary processing with use of the respective threshold values. At sequent step S4, it is executed to extract the surface defects B1, B2 and the routine is ended. In this way, defect-extraction images 117A and 117B of the oil-sticking portion Fo and the non-sticking portion Fn can be obtained as shown in FIG. 18.

Further, in the image processing device 103, the above images 117A, 117B are composed to form a composite image 118 by the image composing section 110. Note, the composite image 118 can be formed with ease since the defect-extraction images 117A, 117B have been images subjected to the binary process. Then, the resulting composite image 118 displayed on the display 111 makes it possible to confirm the surface defects B1, B2 by the single image with ease.

In this way, the surface inspecting apparatus of the embodiment is simple in structure and compact in comparison with the conventional inspecting apparatus, thereby facilitating its installation in the pressing line remarkably. Furthermore, the surface inspecting apparatus allows the surface F of the body panel P crowded with the oil-sticking portions Fo and the non-sticking portions Fn and the curved surface F to be inspected in just the state it is, certainly.

Again, since the conventional step to apply oil to the surface F is abolished in this surface inspecting apparatus, it is possible to carry out the successive inspection in the pressing line where the formed body panels P are conveyed in turn, rapidly, thereby contributing the reduction of time for inspection and the reduction in cost.

Moreover, since both imaging (pickup) and image processing are successively carried out while moving the surface F to one direction at the fixed speed by the conveying unit 104, it is possible to display the image on the display 111 of the image processing device 103 as if it were a moving picture captured by the single camera.

Additionally, while the surface profile (inclination) of the surface F at the imaging position changes every moment because of its curved configuration, it is possible to always keep both emitting angle θs and imaging angle θc against the surface F constant since the drive control unit 114 does control the directions of the emitting units L1, L2 and the cameras C1, C2 on the basis of the signals from the position detecting unit 112 and the profile output section 113. Consequently, as the imaging (pickup) condition relative to the curved surface F is maintained regularly, it becomes possible to establish the surface inspecting apparatus in the pressing line and detect the surface defects on the body panel P with high detection ratio, automatically.

Note, when using two emitting units L1, L2 and two cameras C1, C2 as the above-mentioned embodiment, it is not always required to respectively dispose these elements L1, L2 and C1, C2 in series so long as two emitting (imaging) areas are so separated as not to interfere with each other.

We now describe a modification of the above-mentioned embodiment.

Although the illuminating device 101 has a function to control the light value (quantity of emission) so as to correspond to the respective reflectivities of the oil-sticking portion Fo and the non-sticking portion Fn in the above-mentioned embodiment, the image input device 102 may have the same function in the modification.

In detail, while the light values of the emitting units L1, L2 constituting the illuminating device 101 are established large so as to correspond to the light reflectivity of the oil-sticking portion Fo, the irises of the first and second cameras C1, C2 constituting the image input device 102 are differentiated from each other. In this case, the first camera C1 has a small iris so as to correspond to the small light reflectivity of the oil-sticking portion Fo, while the first camera C2 has a large iris so as to correspond to the large light reflectivity of the non-sticking portion Fn.

According to the surface inspecting apparatus constructed above, in the original image 116A obtained by the first camera C1 with the small iris, there exists an unclear image of the non-sticking portion Fn of high (large) reflectivity under the saturated condition due to a large quantity of light received by the first camera C1 and a clear image of the oil-sticking portion Fo having low (small) reflectivity. While, in the original image 116B obtained by the second camera C2 having a large iris established, there exists an unclear image of the oil-sticking portion Fo of low reflectivity due to a small quantity of light received by the second camera C2 and a clear image of the non-sticking portion Fn having high reflectivity.

Therefore, also in the above-mentioned surface inspecting apparatus, it is possible to obtain the extracted defect images 117A, 117B and the composite image 118 by accomplishing the image processing for the original images 116A, 116B in the image processing device 103. Additionally, owing to the provision of the conveying unit 104, the position detecting unit 112, the profile output section 113 and the drive control section 114, it is possible to obtain the similar operations and effects to the previous embodiment.

Figure 21:
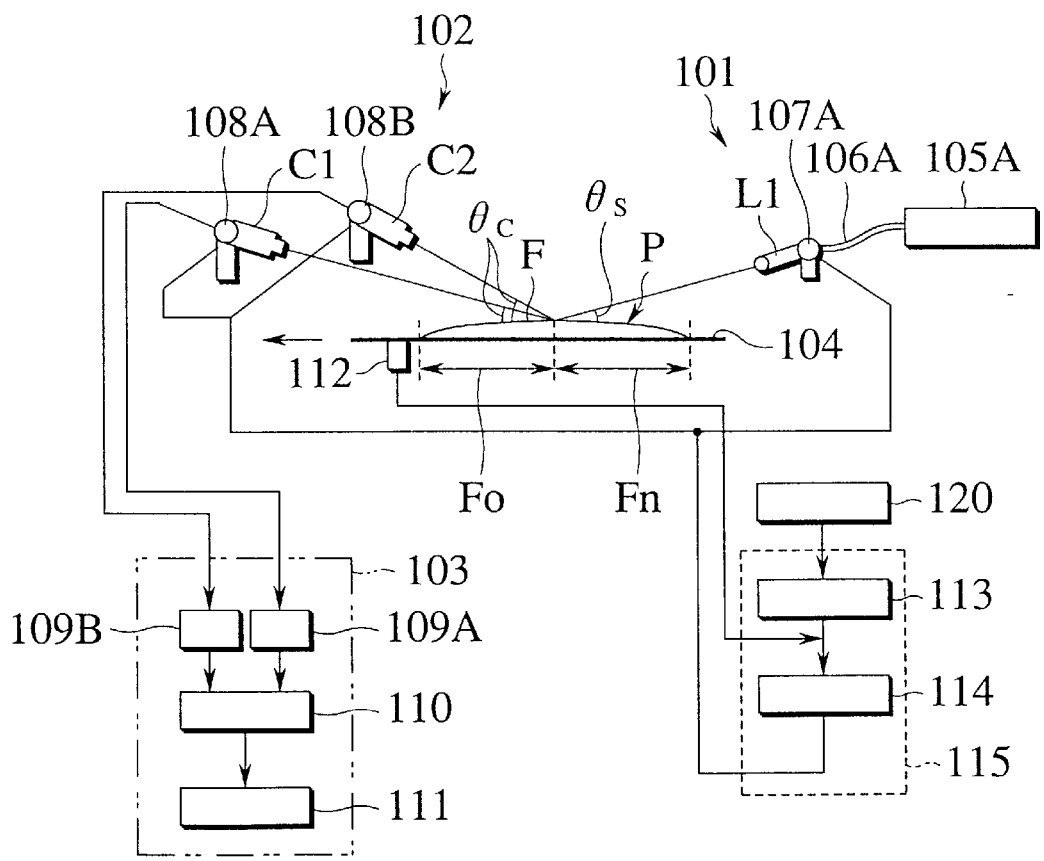
FIG. 21 is a schematic view showing a constitution of a surface inspecting apparatus in accordance with a sixth embodiment of the present invention.
Figure 22:
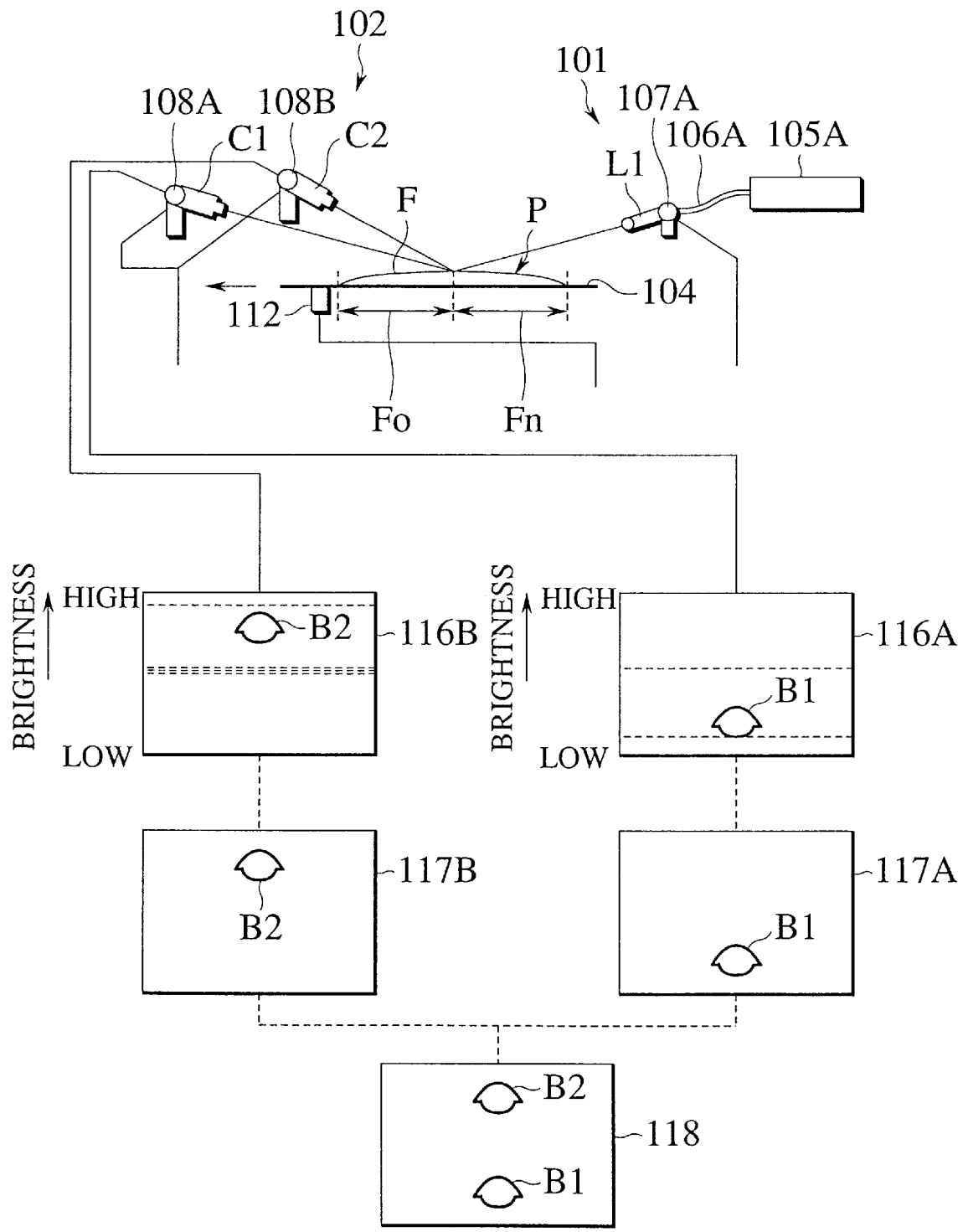
FIG. 22 is an explanation diagram showing various images captured by the surface inspecting apparatus of FIG. 21.

FIGS. 21 and 22 are explanation diagrams of the surface inspecting apparatus in accordance with the other (6th.) embodiment. Note, in this embodiment, elements similar to those of the previously mentioned embodiment are indicated with the same reference numerals respectively and their detailed explanations are eliminated.

The surface inspecting apparatus of FIG. 21 includes the illuminating device 101 composed of a single illuminating unit L1. The emitting unit L1 is established so as to have a large light value corresponding to the reflectivity of the oil-sticking portion Fo on the surface E While, the image input device 102 comprises the first camera C1 of which iris is established small corresponding to low reflectivity of the oil-sticking portion Fo, and the second camera C2 of which iris is established large corresponding to high reflectivity of the non-sticking portion Fn. Further, the imaging positions of both cameras C1, C2 are arranged so as to coincide with the illuminating position by the emitting unit L1.

In this way, when capturing the same position by the first and second cameras C1, C2 on condition that the light value of the illuminating device 101 is constant, it is possible to obtain the original images 116A, 116B of the oil-sticking portion Fo and the non-sticking portion Fn as shown in FIG. 22, and also obtain the extracted defect images 117A, 117B and the composite image 118 by the image processing device 103, as similar to the previous embodiment. Further, due to the single emitting unit L1 of the illuminating device 101, the structure of the surface inspecting apparatus can be simplified and down-sized.

Figure 23:
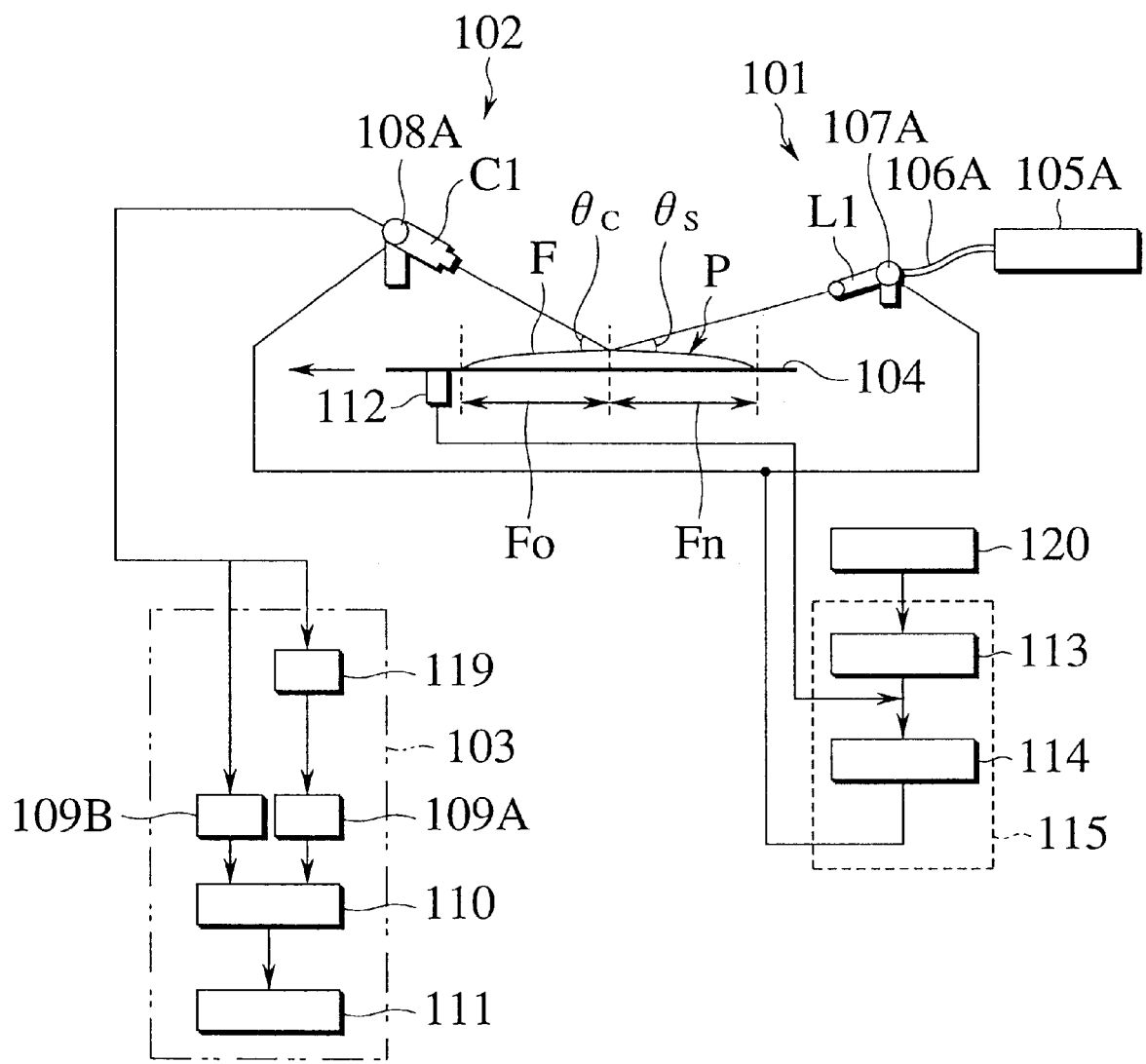
FIG. 23 is a schematic view showing a constitution of a surface inspecting apparatus in accordance with a seventh embodiment of the present invention.
Figure 24:
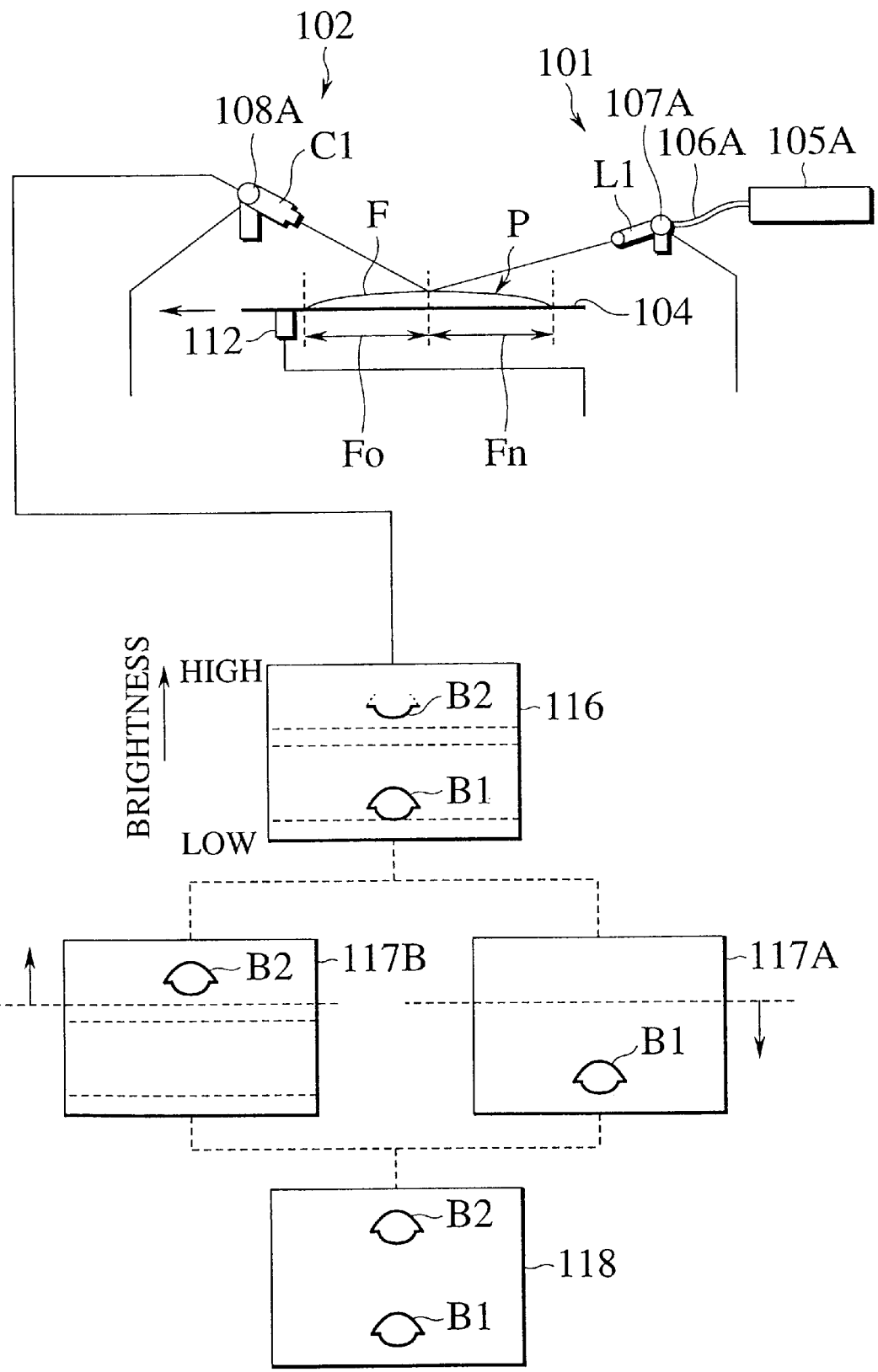
FIG. 24 is an explanation diagram showing various images captured by the surface inspecting apparatus of FIG. 23.

FIGS. 23 and 24 are explanation diagrams of the surface inspecting apparatus in accordance with the other (7th.) embodiment. Note, also in this embodiment, elements similar to those of the previously mentioned embodiment are indicated with the same reference numerals respectively and their detailed explanations are eliminated.

The surface inspecting apparatus shown in FIG. 23 includes the illuminating device 101 for emitting light at the emitting angle θs inclined to the inspected surface F, the image input device 102 opposed to the illuminating device 101 to take a picture of the surface F at the imaging angle θc larger than the emitting angle θs, and the image processing unit 103 which forms the respective images of the oil-sticking portion Fo and the non-sticking portion Fn from the image captured by the image input device 102 on the basis of the detecting sensitivities of the oil-sticking portion Fo and the non-sticking portion Fn thereby to extract the surface defects for each image.

The surface inspecting apparatus of FIG. 23 includes the illuminating device 101 constituted by the single illuminating unit L1 and the image input device 102 constituted by the single camera C1. The emitting unit L1 is established so as to have a large light value corresponding to low reflectivity of the oil-sticking portion Fo on the surface F.

The image processing unit 103 comprises the first and second processing section 109A, 109B, the image composing section 110, the display 111 and an identifying section 119 in front of the first processing section 109A.

As shown in FIG. 24, since the illuminating unit L1 of the illuminating device 101 has a great light value, there contains an image of the non-sticking portion Fn of high reflectivity toward saturation and a clear image of the oil-sticking portion Fo of low reflectivity in the original image 116 captured by the camera C1 of the image input device 102. Note, as the image is captured by the camera C1 of the image input device 102 at the intermediate angle θs, the non-sticking portion Fn is imaged under condition that its saturation area is shifted to the illuminating direction rather than the oil-sticking portion Fo. Thus, the proper adjustments for the pickup (imaging) range and position of the camera C1 allows both oil-sticking portion Fo and non-sticking portion Fn to be captured simultaneously, in spite of an image toward saturation of the non-sticking portion Fn.

In the surface inspecting apparatus of the embodiment, the original image 116 captured in the above way is inputted into the identifying section 119 of the image processing unit 103. The identifying section 19 does identify the oil-sticking portion Fo to judge a boundary between the portion Fo and the non-sticking portion Fn. That is, as mentioned in the previous embodiment, since the reflectivity of the oil-sticking portion Fo is different from that of the non-sticking portion Fn thereby causing a difference in detecting sensitivity, the identifying section 119 takes cognizance of the oil-sticking portion Fo on the basis of the difference in detecting sensitivity (luminance).

The image including the oil-sticking portion Fo identified by the identifying section 119 is inputted into the first processing section 109A. Again, the original image 116 is also inputted into the second processing section 109B. Respectively established in the first processing section 109A and the second processing section 109B are appropriate small threshold value which is founded on a level of low luminance of the oil-sticking portion Fo on the original image 116 and appropriate large threshold value which is founded on a level of high luminance of the non-sticking portion Fn on the original image 116.

Therefore, by the execution of edge extraction in the first and second processing sections 109A, 109B and binary processing by the respective threshold values, there are obtained the extracted-defect image 117A of the oil-sticking portion Fo containing the surface defect B1 and the extracted-defect image 117B of the non-sticking portion Fn containing the surface defect B2, as shown in FIG. 23. Both of the extracted-defect images 117A, 117B is composed to the composite image 118 by the image composing section 118 and displayed on the display 111.

In this way, according to the surface inspecting apparatus of the above embodiment, it is possible to accomplish the similar operations and effects to the previous embodiment owing to the image processing for the oil-sticking portion Fo and the non-sticking portion Fn carried out by the image processing unit 103. Moreover, since the illuminating device 101 and the image input device 102 are constituted by the single emitting unit L1 and the single camera C1 respectively, it is possible to simplify and miniaturize the structure furthermore, thereby facilitating the installation of the surface inspecting apparatus in the pressing line.

Although the identifying section 119 for judging the oil-sticking portion Fo is arranged in front of the first processing section 109A in the above-mentioned embodiment, an identifying section for judging the non-sticking portion Fn may be arranged in front of the second processing section 109B in the modification. Alternatively, both images of the oil-sticking portion Fo and the non-sticking portion Fn judged by the identifying section may be inputted into both of the processing sections 109A, 109B.

Note, although the surface F to be inspected is transported in one direction by the conveying device 104 in the above-mentioned embodiments, the surface inspecting apparatus of the invention is also capable of inspecting the surface under a stable condition, of course. In such a case, it may be adopted to vary the light value at the imaging position by the following methods of:

- using either one of the image input device with adjustable iris or the illuminating device characterized by adjustable light value, thereby differentiating either light value or iris for every image of the oil-sticking portion and the non-sticking portion upon;
- using two illuminating units of different light values or two cameras, thereby switching these operations properly; and
- using two illuminating units to switch between the illumination by the single unit and that by both units.

Finally, it will be understood by those skilled in the art that the foregoing description relates to preferred embodiments of the disclosed surface inspecting apparatus, and that various changes and modifications may be made to the present invention without departing from the spirit and scope thereof.

What is claimed is:

1. A surface inspecting apparatus for inspecting a surface of an object to be inspected, the surface inspecting apparatus comprising:

an illuminating unit for emitting illumination light to the surface of the object;

an imaging unit for taking a picture of the surface of the object illuminated by the illumination light to form an illuminated image of the surface;

an image processing unit for detecting a defect existing on the surface on a basis of the illuminated image obtained by the imaging unit to output detected information about the defect;

a surface-sort inputting unit for inputting a sort of the surface to be inspected;

a surface-position detecting section for detecting positional information about a position of the surface in a transporting direction to transport the object to be inspected;

a surface-information specifying section for specifying a curved profile of the surface and angular information about an angle of inclination of the surface, corresponding to the sort of the surface obtained by the surface-sort inputting unit and the positional information obtained by the surface-position detecting section; and positional relationship controlling section for controlling a positional relationship among the illuminating unit, the imaging unit and the surface to be inspected, on the basis of the angular information specified by the surface-information specifying section and the positional information detected by the surface-position detecting section;

wherein the positional relationship controlling section controls the positional relationship among the illuminating unit, the imaging unit and the surface to be inspected in such a manner that an incident angle of the illumination light on the surface falls within a definite range and the imaging unit receives diffused reflection light of the illumination light reflected by the surface at a reflection angle which is smaller than the incident angle of the illumination light.

2. The surface inspecting apparatus of claim 1, wherein the incident angle of the illumination light is from 80 to 90 degrees, while the reflection angle of the diffused light is from 50 to 75 degrees.

3. The surface inspecting apparatus of claim 1, wherein the positional relationship controlling section comprises:

an emitting angle and position controlling section for controlling both of an emitting angle of the illuminating unit and a height thereof so that the incident angle of the illumination light on the surface falls within the definite range usually; and an imaging angle and position controlling section for controlling both of an imaging angle of the imaging unit and a height thereof so that the imaging unit receives the diffused reflection light of the illumination light reflected at the reflection angle smaller than the incident angle of the illumination light.

4. The surface inspecting apparatus of claim 3, further comprising a setting angle inputting unit into which a setting inclination angle of the object is inputted when the object is transported, wherein the surface-information specifying section specifies the curved profile of the surface and the angular information about the angle of inclination of the surface, corresponding to the sort of the surface obtained by the surface-sort inputting unit, angular information of the object obtained by the setting angle inputting unit and the positional information obtained by the surface-position detecting section.

5. The surface inspecting apparatus of claim 3, wherein the illuminating unit includes:
a front illuminating unit for illuminating a front side of the surface to be inspected in the transporting direction; and
a rear illuminating unit for illuminating a rear side of the surface to be inspected in the transporting direction;

and the imaging unit includes:
a front imaging unit for taking a picture of the front side of the surface in the transporting direction on the basis of the reflection light from the surface; and
a rear imaging unit for taking a picture of the rear side of the surface in the transporting direction on the basis of the reflection light from the surface;

said surface inspecting device further comprising a front-to-back illuminating and imaging switching section which carries out a switching in operation between the front illuminating unit and the rear illuminating unit and another switching in operation between the front imaging unit and the rear imaging unit.

6. The surface inspecting apparatus of claim 3, wherein the illuminating unit comprises a linear light source and the imaging unit comprises a CCD camera.

7. The surface inspecting apparatus of claim 3, wherein at least either one of the illuminating unit and the imaging unit has a light-quantity adjusting function which is capable of coping with respective reflectivities of light at an oil-sticking portion and a non-sticking portion on the surface of the object.

8. The surface inspecting apparatus of claim 7, wherein the imaging unit comprises a first camera having an iris adjusted corresponding to the reflectivity of light at the oil-sticking portion and a second camera having an iris adjusted corresponding to the reflectivity of light at the non-sticking portion and the first and second cameras are so arranged as to respectively provide first and second imaging positions in series along the transporting direction of the surface to be inspected.

9. The surface inspecting apparatus of claim 7, wherein the imaging unit comprises first and second cameras arranged as to respectively provide first and second imaging positions in series along the transporting direction of the surface to be inspected, while the illuminating unit comprises a first illuminating part having a quantity of light adjusted corresponding to the reflectivity of the oil-sticking portion and a second illuminating part having a quantity of light adjusted corresponding to the reflectivity of the non-sticking portion; and wherein the first and second illuminating parts are arranged so that first and second illuminating positions thereof correspond to the first and second imaging positions, respectively.

10. The surface inspecting apparatus of claim 7, wherein the image processing unit has a function to combine a defect-image extracted from the oil-sticking portion with another defect-image extracted from the non-sticking portion.

11. The surface inspecting apparatus of claim 1, wherein the positional relationship controlling section comprises a surface angle and position control section for controlling an inclination angle and a height of the surface to be inspected in such a manner that both of an emitting angle of the illuminating unit and an imaging angle of the imaging unit usually fall within definite ranges, respectively.

12. The surface inspecting apparatus of claim 11, wherein the illuminating unit comprises a linear light source and the imaging unit comprises a CCD camera.

13. The surface inspecting apparatus of claim 11, wherein at least either one of the illuminating unit and the imaging unit has a light-quantity adjusting function which is capable of coping with respective reflectivities of light at an oil-sticking portion and a non-sticking portion on the surface of the object.

14. The surface inspecting apparatus of claim 13, wherein the imaging unit comprises a first camera having an iris adjusted corresponding to the reflectivity of light at the oil-sticking portion and a second camera having an iris adjusted corresponding to the reflectivity of light at the non-sticking portion and the first and second cameras are so arranged as to respectively provide first and second imaging positions in series along the transporting direction of the surface to be inspected.

15. The surface inspecting apparatus of claim 13, wherein the imaging unit comprises first and second cameras arranged as to respectively provide first and second imaging positions in series along the transporting direction of the surface to be inspected, while the illuminating unit comprises a first illuminating part having a quantity of light adjusted corresponding to the reflectivity of the oil-sticking portion and a second illuminating part having a quantity of light adjusted corresponding to the reflectivity of the non-sticking portion; and wherein the first and second illuminating parts are arranged so that first and second illuminating positions thereof correspond to the first and second imaging positions, respectively.

16. The surface inspecting apparatus of claim 13, wherein the inspecting unit has a function to combine a defect-image extracted from the oil-sticking portion with another defect-image extracted from the non-sticking portion.

* * * * *